United States Patent
Jensen

(10) Patent No.: US 11,155,783 B2
(45) Date of Patent: *Oct. 26, 2021

(54) TRUNCATED EPIDERIMAL GROWTH FACTOR RECEPTOR (EGFRT) FOR TRANSDUCED T CELL SELECTION

(71) Applicant: City of Hope, Duarte, CA (US)

(72) Inventor: Michael C. Jensen, Duarte, CA (US)

(73) Assignee: City of Hope, Duarte, CA (US)

( * ) Notice: Subject to any disclaimer, the term of this patent is extended or adjusted under 35 U.S.C. 154(b) by 476 days.

This patent is subject to a terminal disclaimer.

(21) Appl. No.: 16/160,944

(22) Filed: Oct. 15, 2018

(65) Prior Publication Data

US 2019/0276801 A1 Sep. 12, 2019

Related U.S. Application Data

(60) Continuation of application No. 15/431,248, filed on Feb. 13, 2017, now Pat. No. 10,100,281, which is a division of application No. 14/340,512, filed on Jul. 24, 2014, now Pat. No. 9,580,685, which is a division of application No. 13/463,247, filed on May 3, 2012, now Pat. No. 8,802,374, which is a continuation of application No. PCT/US2010/055329, filed on Nov. 3, 2010.

(60) Provisional application No. 61/257,567, filed on Nov. 3, 2009.

(51) Int. Cl.
| | |
|---|---|
| *C12N 5/0783* | (2010.01) |
| *C07K 14/71* | (2006.01) |
| *A61K 35/17* | (2015.01) |
| *C12N 9/12* | (2006.01) |

(52) U.S. Cl.
CPC ............ *C12N 5/0636* (2013.01); *A61K 35/17* (2013.01); *C07K 14/71* (2013.01); *C12N 9/12* (2013.01); *C12N 2510/00* (2013.01); *C12Y 207/10001* (2013.01)

(58) Field of Classification Search
None
See application file for complete search history.

(56) References Cited

U.S. PATENT DOCUMENTS

| | | | |
|---|---|---|---|
| 5,753,462 A | 5/1998 | Lok | |
| 6,790,614 B1 | 9/2004 | Pippig et al. | |
| 2004/0126363 A1 | 7/2004 | Jensen et al. | |
| 2005/0003484 A1 | 1/2005 | Hirano et al. | |
| 2005/0053608 A1 | 3/2005 | Weber et al. | |
| 2012/0301447 A1 | 11/2012 | Jensen | |
| 2015/0184128 A1 | 7/2015 | Jensen | |
| 2017/0152480 A1 | 6/2017 | Jensen | |

FOREIGN PATENT DOCUMENTS

WO   WO2006009694   1/2006

OTHER PUBLICATIONS

European Search Report in European Application No. 19150829.0, dated May 22, 2019, 8 pages.
Baron et al, "Soluble epidermal growth factor receptor (sEGFR/sErbB1) as a potential risk, screening, and diagnostic serum biomarker of epithelial ovarian cancer," Cancer, Epidemiology, Biomarkers and Prevention, 2003, 12(2):103-113.
Müller et al, "Prognostic and Predictive Impact of Soluble Epidermal Growth Factor Receptor (sEGFR) Protein in the Serum of Patients Treated With Chemotherapy for Metastatic Breast Cancer," Anticancer Research, 2006, 26(2B):1479-1487.
Petch et al, "A truncated, secreted form of the epidermal growth factor receptor is encoded by an alternatively spliced transcript in normal rat tissue," Molecular and Cellular Biology, 1990, 10(6):2973-2982.
Berger et al., "Analysis of Transgene-Specific Immune Responses that Limit the In Vivo Persistence of Adoptively Transferred HSV-TK-Modified Donor T Cells After Allogeneic Hematoppoietic Cell Transplantation", Blood 107(6):2294-2302 (2006).
Chakraverty et al., "An Inflammatory Checkpoint Regulates Recruitment of Graft-Versus-Host Reactive TCells to Peripheral Tissues", J. Exp. Med. 203(8):2021-2031 (2006).
Dawson et al., Epidermal Growth Factor Receptor Dimerization and Activation Require Ligand-Induced Induced Conformational Changes in the Dimer Interface, Mol. Cell. Biol. 25(17):7734-7742 (2005).

(Continued)

*Primary Examiner* — Christopher M Babic
*Assistant Examiner* — Kimberly A Aron
(74) *Attorney, Agent, or Firm* — Fish & Richardson P.C.

(57) ABSTRACT

A non-immunogenic selection epitope may be generated by removing certain amino acid sequences of the protein. For example, a gene encoding a truncated human epidermal growth factor receptor polypeptide (EGFRt) that lacks the membrane distal EGF-binding domain and the cytoplasmic signaling tail, but retains an extracellular epitope recognized by an anti-EGFR antibody is provided. Cells may be genetically modified to express EGFRt and then purified without the immunoactivity that would accompany the use of full-length EGFR immunoactivity. Through flow cytometric analysis, EGFRt was successfully utilized as an in vivo tracking marker for genetically modified human T cell engraftment in mice. Furthermore, EGFRt was demonstrated to have cellular depletion potential through cetuximab mediated antibody dependent cellular cytotoxicity (ADCC) pathways. Thus, EGFRt may be used as a non-immunogenic selection tool, tracking marker, a depletion tool or a suicide gene for genetically modified cells having therapeutic potential.

20 Claims, 19 Drawing Sheets

Specification includes a Sequence Listing.

(56) References Cited

OTHER PUBLICATIONS

European Patent Office, Extended European Search Report and Opinion dated May 31, 2013 for Application No. 10829041.2.
Fehse et al., "Selective Immunoaffinity-Based Enrichment of CD34+ Cells Transduced with Retroviral Vectors Containing an Intracytoplasmatically Truncated Version of the Human Low-Affinity Nerve Growth Factor Receptor (deltaLNGFR) Gene", Human Gene Ther. 8:1815-1824.
Fehse et al., "CD34 Splice Variant: An Attractive Marker for Selection of Gene-Modified Cells", Mol. Ther. 1(5):448-456 (2000).
Gaines et al., "p1RES-CD41, A Dicistronic Expression Vector for MACS- or FACS-Based Selection of Transfected Cells", BioTechniques 26:683-688 (1999).
Khoda et al., "A 40-kDaEpidermal Growth Factor/Transforming Growth Factor alpha-Binding Domain Produced by Limited Proteolysis of the Extracellular Domain of the Epidermal Growth Factor Receptor", The Journal of Biological Chemistry, 1993, 268(3):1976-1981.
Kil Sj et al., "A leucine-based determinant in the epidermal growth factor receptor juxtamembrane domain is required for the efficient transport of ligand-receptor complexes to lysosomes," The Journal of Biological Chemistry, Jan. 29, 1999, 274(5):3141-3150.
Kowolik et al., "CD28 Costimulation Provided Through a CD19-Specific Chimeric Antigen Receptor Enhances In Vivo Persistence and Antitumor Efficacy of Adoptively Transferred T Cells", Cancer Res. 66:10995-11004 (2006).
Lange et al., "CD34 Modulates the Trafficking Behavior of Hematopoietic Cells In Vivo", Stem Cells and Development 16:297-304 (2007).
Lemoine et al., "Efficient Transduction and Selection of Human T-Lymphocytes with Bicistronic Thy1/HSV1-TK Retroviral Vector Produced by a Human Packaging Cell Line", J. Gene Med. 6:374-386 (2004).
Li et al., "Structural Basis for Inhibition of the Epidermal Growth Factor Receptor by Cetuximab", Cancer Cell 7:302-311 (2005).
Pelloquin et al., "Human Blymphocytes Immortalization by Epstein-Barr Virus in the Presence of Cyclosporin A", In Vitro Cell Devel. Biol. 22(12):689-694 (1986).
Powell, et al., "Large-Scale Depletion of CD25+ Regulatory T Cells from Patient Leukapheresis Samples", J. Immunother. 28(4):403-411 (2005).
Singh et al., :"Redirecting Specificity of T-cell Populations for CD19 Using the Sleeping Beauty System", Cancer Research, 2008, 68:2961-2971.
Szymczak et al., "Correction of Multi-Gene Deficiency In Vivo using a Single 'Self-Cleaving' 2A Peptide-Based Retroviral Vector", Nat. Biotech. 22(5):589-594 (2004).
Tey et al., Inducible Caspase 9 Suicide Gene to Improve the Safety of Allodepleted T Cells.
United States Patent and Trademark Office, International Search Report and Written Opinion dated Apr. 7, 2011 for PCT/US10/55329.
Wang, X., et al., "A Transgene-Encoded Cell Surface Polypeptide for Selection, in Vivo Tracking, and Ablation of Engineered Cells," Blood 118:1255-1263 (2011).
Yam et al., "Ex Vivo Selection and Expansion of Cells Based on Expression of a Mutated Inosine monophosphate Dehydrogenase 2 After HIV Vector Transduction: Effects on Lymphocytes, Monocytes, and CD34+ Stem Cells", Mol. Ther. 14(2):236-244 (2006).
Ferguson, "A structure-based view of Epidermal Growth Factor Receptor Regulation," 2008, 37:353-373.

Figure 7

```
            M   L   L   V   T   S   L   L   L   C   E   L   P   H   P   A   F   L   L
   1 ATGCTTCTCC TGGTGACAAG CCTTCTGCTC TGTGAGTTAC CACACCCAGC ATTCCTCCTG
     TACGAAGAGG ACCACTGTTC GGAAGACGAG ACACTCAATG GTGTGGGTCG TAAGGAGGAC
            I   P   R   K   V   C   N   G   I   G   I   G   E   F   K   D   S   L   S   I
  61 ATCCCACGCA AAGTGTGTAA CGGAATAGGT ATTGGTGAAT TTAAAGACTC ACTCTCCATA
     TAGGGTGCGT TTCACACATT GCCTTATCCA TAACCACTTA AATTTCTGAG TGAGAGGTAT
            N   A   T   N   I   K   H   F   K   N   C   T   S   I   S   G   D   L   H   I
 121 AATGCTACGA ATATTAAACA CTTCAAAAAC TGCACCTCCA TCAGTGGCGA TCTCCACATC
     TTACGATGCT TATAATTTGT GAAGTTTTTG ACGTGGAGGT AGTCACCGCT AGAGGTGTAG
            L   P   V   A   F   R   G   D   S   F   T   H   T   P   P   L   D   P   Q   E
 181 CTGCCGGTGG CATTTAGGGG TGACTCCTTC ACACATACTC CTCCTCTGGA TCCACAGGAA
     GACGGCCACC GTAAATCCCC ACTGAGGAAG TGTGTATGAG GAGGAGACCT AGGTGTCCTT
            L   D   I   L   K   T   V   K   E   I   T   G   F   L   L   I   Q   A   W   P
 241 CTGGATATTC TGAAAACCGT AAAGGAAATC ACAGGGTTTT TGCTGATTCA GGCTTGGCCT
     GACCTATAAG ACTTTTGGCA TTTCCTTTAG TGTCCCAAAA ACGACTAAGT CCGAACCGGA
            E   N   R   T   D   L   H   A   F   E   N   L   E   I   R   G   R   T   K
 301 GAAAACAGGA CGGACCTCCA TGCCTTTGAG AACCTAGAAA TCATACGCGG CAGGACCAAG
     CTTTTGTCCT GCCTGGAGGT ACGGAAACTC TTGGATCTTT AGTATGCGCC GTCCTGGTTC
            Q   H   G   Q   F   S   L   A   V   V   S   L   N   I   T   S   L   G   L   R
 361 CAACATGGTC AGTTTTCTCT TGCAGTCGTC AGCCTGAACA TAACATCCTT GGGATTACGC
     GTTGTACCAG TCAAAAGAGA ACGTCAGCAG TCGGACTTGT ATTGTAGGAA CCCTAATGCG
            S   L   K   E   I   S   D   G   D   V   I   I   S   G   N   K   N   L   C   Y
 421 TCCCTCAAGG AGATAAGTGA TGGAGATGTG ATAATTTCAG GAAACAAAAA TTTGTGCTAT
     AGGGAGTTCC TCTATTCACT ACCTCTACAC TATTAAAGTC CTTTGTTTTT AAACACGATA
            A   N   T   I   N   W   K   K   L   F   G   T   S   G   Q   K   T   K   I   I
 481 GCAAATACAA TAAACTGGAA AAAACTGTTT GGGACCTCCG GTCAGAAAAC CAAAATTATA
     CGTTTATGTT ATTTGACCTT TTTTGACAAA CCCTGGAGGC CAGTCTTTTG GTTTTAATAT
            S   N   R   G   E   N   S   C   K   A   T   G   Q   V   C   H   A   L   C   S
 541 AGCAACAGAG GTGAAAACAG CTGCAAGGCC ACAGGCCAGG TCTGCCATGC CTTGTGCTCC
     TCGTTGTCTC CACTTTTGTC GACGTTCCGG TGTCCGGTCC AGACGGTACG GAACACGAGG
            P   E   G   C   W   G   P   E   P   R   D   C   V   S   C   R   N   V   S   R
 601 CCCGAGGGCT GCTGGGGCCC GGAGCCCAGG GACTGCGTCT CTTGCCGGAA TGTCAGCCGA
     GGGCTCCCGA CGACCCCGGG CCTCGGGTCC CTGACGCAGA GAACGGCCTT ACAGTCGGCT
            G   R   E   C   V   D   K   C   N   L   L   E   G   E   P   R   E   F   V   E
 661 GGCAGGGAAT GCGTGGACAA GTGCAACCTT CTGGAGGGTG AGCCAAGGGA GTTTGTGGAG
     CCGTCCCTTA CGCACCTGTT CACGTTGGAA GACCTCCCAC TCGGTTCCCT CAAACACCTC
            N   S   E   C   I   Q   C   H   P   E   C   L   P   Q   A   M   N   I   T   C
 721 AACTCTGAGT GCATACAGTG CCACCCAGAG TGCCTGCCTC AGGCCATGAA CATCACCTGC
     TTGAGACTCA CGTATGTCAC GGTGGGTCTC ACGGACGGAG TCCGGTACTT GTAGTGGACG
            T   G   R   G   P   D   N   C   I   Q   C   A   H   Y   I   D   G   P   H   C
 781 ACAGGACGGG GACCAGACAA CTGTATCCAG TGTGCCCACT ACATTGACGG CCCCCACTGC
     TGTCCTGCCC CTGGTCTGTT GACATAGGTC ACACGGGTGA TGTAACTGCC GGGGGTGACG
            V   K   T   C   P   A   G   V   M   G   E   N   N   T   L   V   W   K   Y   A
 841 GTCAAGACCT GCCCGGCAGG AGTCATGGGA GAAAACAACA CCCTGGTCTG GAAGTACGCA
     CAGTTCTGGA CGGGCCGTCC TCAGTACCCT CTTTTGTTGT GGGACCAGAC CTTCATGCGT
            D   A   G   H   V   C   H   L   C   H   P   N   C   T   Y   G   C   T   G   P
 901 GACGCCGGCC ATGTGTGCCA CCTGTGCCAT CCAAACTGCA CCTACGGATG CACTGGGCCA
     CTGCGGCCGG TACACACGGT GGACACGGTA GGTTTGACGT GGATGCCTAC GTGACCCGGT
            G   L   E   G   C   P   T   N   G   P   K   I   P   S   I   A   T   G   M   V
 961 GGTCTTGAAG GCTGTCCAAC GAATGGGCCT AAGATCCCGT CCATCGCCAC TGGGATGGTG
     CCAGAACTTC CGACAGGTTG CTTACCCGGA TTCTAGGGCA GGTAGCGGTG ACCCTACCAC
            G   A   L   L   L   L   V   V   A   L   G   I   G   L   F   M
1021 GGGGCCCTCC TCTTGCTGCT GGTGGTGGCC CTGGGGATCG GCCTCTTCAT G
     CCCCGGGAGG AGAACGACGA CCACCACCGG GACCCCTAGC CGGAGAAGTA C
```

Figure 8    CD19R-CD28gg-Zeta(CO)-T2A-EGFRt

```
          M   L   L   V   T   S   L   L   L   C   E   L   P   H   P   A   F   L   L
   1 ATGCTGCTGC TGGTGACCAG CCTGCTGCTG TGCGAGCTGC CCCACCCCGC CTTTCTGCTG
     TACGACGACG ACCACTGGTC GGACGACGAC ACGCTCGACG GGGTGGGGCG GAAAGACGAC
          I   P   D   I   Q   M   T   Q   T   T   S   S   L   S   A   S   L   G   D   R
  61 ATCCCCGACA TCCAGATGAC CCAGACCACC TCCAGCCTGA GCGCCAGCCT GGGCGACCGG
     TAGGGGCTGT AGGTCTACTG GGTCTGGTGG AGGTCGGACT CGCGGTCGGA CCCGCTGGCC
          V   T   I   S   C   R   A   S   Q   D   I   S   K   Y   L   N   W   Y   Q   Q
 121 GTGACCATCA GCTGCCGGGC CAGCCAGGAC ATCAGCAAGT ACCTGAACTG GTATCAGCAG
     CACTGGTAGT CGACGGCCCG GTCGGTCCTG TAGTCGTTCA TGGACTTGAC CATAGTCGTC
          K   P   D   G   T   V   K   L   L   I   Y   H   T   S   R   L   H   S   G   V
 181 AAGCCCGACG GCACCGTCAA GCTGCTGATC TACCACACCA GCCGGCTGCA CAGCGGCGTG
     TTCGGGCTGC CGTGGCAGTT CGACGACTAG ATGGTGTGGT CGGCCGACGT GTCGCCGCAC
          P   S   R   F   S   G   S   G   S   G   T   D   Y   S   L   T   I   S   N   L
 241 CCCAGCCGGT TTAGCGGCAG CGGCTCCGGC ACCGACTACA GCCTGACCAT CTCCAACCTG
     GGGTCGGCCA AATCGCCGTC GCCGAGGCCG TGGCTGATGT CGGACTGGTA GAGGTTGGAC
          E   Q   E   D   I   A   T   Y   F   C   Q   Q   G   N   T   L   P   Y   T   F
 301 GAACAGGAAG ATATCGCCAC CTACTTTTGC CAGCAGGGCA ACACACTGCC CTACACCTTT
     CTTGTCCTTC TATAGCGGTG GATGAAAACG GTCGTCCCGT TGTGTGACGG GATGTGGAAA
          G   G   G   T   K   L   E   I   T   G   S   T   S   G   S   G   K   P   G   S
 361 GGCGGCGGAA CAAAGCTGGA AATCACCGGC AGCACCTCCG GCAGCGGCAA GCCTGGCAGC
     CCGCCGCCTT GTTTCGACCT TTAGTGGCCG TCGTGGAGGC CGTCGCCGTT CGGACCGTCG
          G   E   G   S   T   K   G   E   V   K   L   Q   E   S   G   P   G   L   V   A
 421 GGCGAGGGCA GCACCAAGGG CGAGGTGAAG CTGCAGGAAA GCGGCCCTGG CCTGGTGGCC
     CCGCTCCCGT CGTGGTTCCC GCTCCACTTC GACGTCCTTT CGCCGGGACC GGACCACCGG
          P   S   Q   S   L   S   V   T   C   T   V   S   G   V   S   L   P   D   Y   G
 481 CCCAGCCAGA GCCTGAGCGT GACCTGCACC GTGAGCGGCG TGAGCCTGCC CGACTACGGC
     GGGTCGGTCT CGGACTCGCA CTGGACGTGG CACTCGCCGC ACTCGGACGG GCTGATGCCG
          V   S   W   I   R   Q   P   P   R   K   G   L   E   W   L   G   V   I   W   G
 541 GTGAGCTGGA TCCGGCAGCC CCCCAGGAAG GGCCTGGAAT GGCTGGGCGT GATCTGGGGC
     CACTCGACCT AGGCCGTCGG GGGGTCCTTC CCGGACCTTA CCGACCCGCA CTAGACCCCG
          S   E   T   T   Y   Y   N   S   A   L   K   S   R   L   T   I   I   K   D   N
 601 AGCGAGACCA CCTACTACAA CAGCGCCCTG AAGAGCCGGC TGACCATCAT CAAGGACAAC
     TCGCTCTGGT GGATGATGTT GTCGCGGGAC TTCTCGGCCG ACTGGTAGTA GTTCCTGTTG
          S   K   S   Q   V   F   L   K   M   N   S   L   Q   T   D   D   T   A   I   Y
 661 AGCAAGAGCC AGGTGTTCCT GAAGATGAAC AGCCTGCAGA CCGACGACAC CGCCATCTAC
     TCGTTCTCGG TCCACAAGGA CTTCTACTTG TCGGACGTCT GGCTGCTGTG GCGGTAGATG
          Y   C   A   K   H   Y   Y   Y   G   G   S   Y   A   M   D   Y   W   G   Q   G
 721 TACTGCGCCA AGCACTACTA CTACGGCGGC AGCTACGCCA TGGACTACTG GGGCCAGGGC
     ATGACGCGGT TCGTGATGAT GATGCCGCCG TCGATGCGGT ACCTGATGAC CCCGGTCCCG
          T   S   V   T   V   S   S   E   S   K   Y   G   P   P   C   P   P   C   P   A
 781 ACCAGCGTGA CCGTGAGCAG CGAGAGCAAG TACGGCCCTC CCTGCCCCCC TTGCCCTGCC
     TGGTCGCACT GGCACTCGTC GCTCTCGTTC ATGCCGGGAG GGACGGGGGG AACGGGACGG
          P   E   F   L   G   G   P   S   V   F   L   F   P   P   K   P   K   D   T   L
 841 CCCGAGTTCC TGGGCGGACC CAGCGTGTTC CTGTTCCCCC CCAAGCCCAA GGACACCCTG
     GGGCTCAAGG ACCCGCCTGG GTCGCACAAG GACAAGGGGG GGTTCGGGTT CCTGTGGGAC
          M   I   S   R   T   P   E   V   T   C   V   V   V   D   V   S   Q   E   D   P
 901 ATGATCAGCC GGACCCCCGA GGTGACCTGC GTGGTGGTGG ACGTGAGCCA GGAAGATCCC
     TACTAGTCGG CCTGGGGGCT CCACTGGACG CACCACCACC TGCACTCGGT CCTTCTAGGG
          E   V   Q   F   N   W   Y   V   D   G   V   E   V   H   N   A   K   T   K   P
 961 GAGGTCCAGT TCAATTGGTA CGTGGACGGC GTGGAAGTGC ACAACGCCAA GACCAAGCCC
     CTCCAGGTCA AGTTAACCAT GCACCTGCCG CACCTTCACG TGTTGCGGTT CTGGTTCGGG

R   E   E   Q   F   N   S   T   Y   R   V   V   S   V   L   T   V   L   H   Q
1021 AGAGAGGAAC AGTTCAACAG CACCTACCGG GTGGTGTCTG TGCTGACCGT GCTGCACCAG
```

Fig. 8 (cont.)

```
                TCTCTCCTTG TCAAGTTGTC GTGGATGGCC CACCACAGAC ACGACTGGCA CGACGTGGTC
                 D  W  L  N  G  K  E  Y  K  C  K  V  S  N  K  G  L  P  S  S
      1081 GACTGGCTGA ACGGCAAAGA ATACAAGTGC AAGGTGTCCA ACAAGGGCCT GCCCAGCAGC
           CTGACCGACT TGCCGTTTCT TATGTTCACG TTCCACAGGT TGTTCCCGGA CGGGTCGTCG
                 I  E  K  T  I  S  K  A  K  G  Q  P  R  E  P  Q  V  Y  T  L
      1141 ATCGAAAAGA CCATCAGCAA GGCCAAGGGC CAGCCTCGCG AGCCCCAGGT GTACACCCTG
           TAGCTTTTCT GGTAGTCGTT CCGGTTCCCG GTCGGAGCGC TCGGGGTCCA CATGTGGGAC
                 P  P  S  Q  E  E  M  T  K  N  Q  V  S  L  T  C  L  V  K  G
      1201 CCTCCCTCCC AGGAAGAGAT GACCAAGAAC CAGGTGTCCC TGACCTGCCT GGTGAAGGGC
           GGAGGGAGGG TCCTTCTCTA CTGGTTCTTG GTCCACAGGG ACTGGACGGA CCACTTCCCG
                 F  Y  P  S  D  I  A  V  E  W  E  S  N  G  Q  P  E  N  N  Y
      1261 TTCTACCCCA GCGACATCGC CGTGGAGTGG GAGAGCAACG GCCAGCCTGA GAACAACTAC
           AAGATGGGGT CGCTGTAGCG GCACCTCACC CTCTCGTTGC CGGTCGGACT CTTGTTGATG
                 K  T  T  P  V  L  D  S  D  G  S  F  F  L  Y  S  R  L  T
      1321 AAGACCACCC CTCCCGTGCT GGACAGCGAC GGCAGCTTCT TCCTGTACAG CCGGCTGACC
           TTCTGGTGGG GAGGGCACGA CCTGTCGCTG CCGTCGAAGA AGGACATGTC GGCCGACTGG
                 V  D  K  S  R  W  Q  E  G  N  V  F  S  C  S  V  M  H  E  A
      1381 GTGGACAAGA GCCGGTGGCA GGAAGGCAAC GTCTTTAGCT GCAGCGTGAT GCACGAGGCC
           CACCTGTTCT CGGCCACCGT CCTTCCGTTG CAGAAATCGA CGTCGCACTA CGTGCTCCGG
                 L  H  N  H  Y  T  Q  K  S  L  S  L  S  L  G  K  M  F  W  V
      1441 CTGCACAACC ACTACACCCA GAAGAGCCTG AGCCTGTCCC TGGGCAAGAT GTTCTGGGTG
           GACGTGTTGG TGATGTGGGT CTTCTCGGAC TCGGACAGGG ACCCGTTCTA CAAGACCCAC
                 L  V  V  V  G  G  V  L  A  C  Y  S  L  L  V  T  V  A  F  I
      1501 CTGGTGGTGG TGGGCGGGGT GCTGGCCTGC TACAGCCTGC TGGTGACAGT GGCCTTCATC
           GACCACCACC ACCCGCCCCA CGACCGGACG ATGTCGGACG ACCACTGTCA CCGGAAGTAG
                 I  F  W  V  R  S  K  R  S  R  G  G  H  S  D  Y  M  N  M  T
      1561 ATCTTTTGGG TGCGGAGCAA GCGGAGCAGA GGCGGCCACA GCGACTACAT GAACATGACC
           TAGAAAACCC ACGCCTCGTT CGCCTCGTCT CCGCCGGTGT CGCTGATGTA CTTGTACTGG
                 P  R  R  P  G  P  T  R  K  H  Y  Q  P  Y  A  P  P  R  D  F
      1621 CCCAGACGGC CTGGCCCCAC CCGGAAGCAC TACCAGCCCT ACGCCCCACC CAGGGACTTT
           GGGTCTGCCG GACCGGGGTG GGCCTTCGTG ATGGTCGGGA TGCGGGGTGG GTCCCTGAAA
                 A  A  Y  R  S  G  G  G  R  V  K  F  S  R  S  A  D  A  P  A
      1681 GCCGCCTACC GGTCCGGCGG AGGGCGGGTG AAGTTCAGCA GAAGCGCCGA CGCCCCTGCC
           CGGCGGATGG CCAGGCCGCC TCCCGCCCAC TTCAAGTCGT CTTCGCGGCT GCGGGGACGG
                 Y  Q  Q  G  Q  N  Q  L  Y  N  E  L  N  L  G  R  R  E  E  Y
      1741 TACCAGCAGG GCCAGAATCA GCTGTACAAC GAGCTGAACC TGGGCAGAAG GGAAGAGTAC
           ATGGTCGTCC CGGTCTTAGT CGACATGTTG CTCGACTTGG ACCCGTCTTC CCTTCTCATG
                 D  V  L  D  K  R  R  G  R  D  P  E  M  G  G  K  P  R  R  K
      1801 GACGTCCTGG ATAAGCGGAG AGGCCGGGAC CCTGAGATGG GCGGCAAGCC TCGGCGGAAG
           CTGCAGGACC TATTCGCCTC TCCGGCCCTG GGACTCTACC CGCCGTTCGG AGCCGCCTTC
                 N  P  Q  E  G  L  Y  N  E  L  Q  K  D  K  M  A  E  A  Y  S
      1861 AACCCCCAGG AAGGCCTGTA TAACGAACTG CAGAAAGACA AGATGGCCGA GGCCTACAGC
           TTGGGGGTCC TTCCGGACAT ATTGCTTGAC GTCTTTCTGT TCTACCGGCT CCGGATGTCG
                 E  I  G  M  K  G  E  R  R  R  G  K  G  H  D  G  L  Y  Q  G
      1921 GAGATCGGCA TGAAGGGCGA GCGGAGGCGG GGCAAGGGCC ACGACGGCCT GTATCAGGGC
           CTCTAGCCGT ACTTCCCGCT CGCCTCCGCC CCGTTCCCGG TGCTGCCGGA CATAGTCCCG
                 L  S  T  A  T  K  D  T  Y  D  A  L  H  M  Q  A  L  P  P  R
      1981 CTGTCCACCG CCACCAAGGA TACCTACGAC GCCCTGCACA TGCAGGCCCT GCCCCCAAGG
           GACAGGTGGC GGTGGTTCCT ATGGATGCTG CGGGACGTGT ACGTCCGGGA CGGGGGTTCC
                 L  E  G  G  G  E  G  R  G  S  L  L  T  C  G  D  V  E  E  N
      2041 CTCGAGGGCG GCGGAGAGGG CAGAGGAAGT CTTCTAACAT GCGGTGACGT GGAGGAGAAT
           GAGCTCCCGC CGCCTCTCCC GTCTCCTTCA GAAGATTGTA CGCCACTGCA CCTCCTCTTA
                 P  G  P  R  M  L  L  L  V  T  S  L  L  L  C  E  L  P  H  P
      2101 CCCGGCCCTA GGATGCTTCT CCTGGTGACA AGCCTTCTGC TCTGTGAGTT ACCACACCCA
```

Fig. 8 (cont.)

```
          GGGCCGGGAT CCTACGAAGA GGACCACTGT TCGGAAGACG AGACACTCAA TGGTGTGGGT
           A  F  L     I  P  R     K  V  C     N  G  I     G  I  E     F  K  D
     2161 GCATTCCTCC TGATCCCACG CAAAGTGTGT AACGGAATAG GTATTGGTGA ATTTAAAGAC
          CGTAAGGAGG ACTAGGGTGC GTTTCACACA TTGCCTTATC CATAACCACT TAAATTTCTG
           S  L  S     I  N  A     T  N  I     K  H  F     K  N  C     T  S  I  S  G
     2221 TCACTCTCCA TAAATGCTAC GAATATTAAA CACTTCAAAA ACTGCACCTC CATCAGTGGC
          AGTGAGAGGT ATTTACGATG CTTATAATTT GTGAAGTTTT TGACGTGGAG GTAGTCACCG
           D  L  H     I  L  P     V  A  F     R  G  D     S  F  T     H  T     P  P  L
     2281 GATCCCACA TCCTGCCGGT GGCATTTAGG GGTGACTCCT TCACACATAC TCCTCCTCTG
          CTAGAGGTGT AGGACGGCCA CCGTAAATCC CCACTGAGGA AGTGTGTATG AGGAGGAGAC
           D  P  Q     E  L  D     I  L  K     T  V  K     E  I  T     G  F     L  L  I
     2341 GATCCACAGG AACTGGATAT TCTGAAAACC GTAAAGGAAA TCACAGGGTT TTTGCTGATT
          CTAGGTGTCC TTGACCTATA AGACTTTTGG CATTTCCTTT AGTGTCCCAA AAACGACTAA
           Q  A  W     P  E  N     R  T  D     L  H  A     F  E  N     L  E     I  I  R
     2401 CAGGCTTGGC CTGAAAACAG GACGGACCTC CATGCCTTTG AGAACCTAGA AATCATACGC
          GTCCGAACCG GACTTTTGTC CTGCCTGGAG GTACGGAAAC TCTTGGATCT TTAGTATGCG
           G  R  T     K  Q  H     G  Q  F     S  L  A     V  V  S     L  N     I  T  S
     2461 GGCAGGACCA AGCAACATGG TCAGTTTTCT CTTGCAGTCG TCAGCCTGAA CATAACATCC
          CCGTCCTGGT TCGTTGTACC AGTCAAAAGA GAACGTCAGC AGTCGGACTT GTATTGTAGG
           L  G  L     R  S  L     K  E  I     S  D  G     D  V  I     I  S     G  N  K
     2521 TTGGGATTAC GCTCCCTCAA GGAGATAAGT GATGGAGATG TGATAATTTC AGGAAACAAA
          AACCCTAATG CGAGGGAGTT CCTCTATTCA CTACCTCTAC ACTATTAAAG TCCTTTGTTT
           N  L  C     Y  A  N     T  I  N     W  K  K     L  F  G     T  S     G  Q  K
     2581 AATTTGTGCT ATGCAAATAC AATAAACTGG AAAAAACTGT TTGGGACCTC CGGTCAGAAA
          TTAAACACGA TACGTTTATG TTATTTGACC TTTTTTGACA AACCCTGGAG GCCAGTCTTT
           T  K  I     I  S  N     R  G  E     N  S  C     K  A  T     G  Q     V  C  H
     2641 ACCAAAATTA TAAGCAACAG AGGTGAAAAC AGCTGCAAGG CCACAGGCCA GGTCTGCCAT
          TGGTTTTAAT ATTCGTTGTC TCCACTTTTG TCGACGTTCC GGTGTCCGGT CCAGACGGTA
           A  L  C     S  P  E     G  C  W     G  P  E     P  R  D     C  V     S  C  R
     2701 GCCTTGTGCT CCCCCGAGGG CTGCTGGGGC CCGGAGCCCA GGGACTGCGT CTCTTGCCGG
          CGGAACACGA GGGGGCTCCC GACGACCCCG GGCCTCGGGT CCCTGACGCA GAGAACGGCC
           N  V  S     R  G  R  E     C  V  D     K  C  N     L  L  E     G     E  P  R
     2761 AATGTCAGCC GAGGCAGGGA ATGCGTGGAC AAGTGCAACC TTCTGGAGGG TGAGCCAAGG
          TTACAGTCGG CTCCGTCCCT TACGCACCTG TTCACGTTGG AAGACCTCCC ACTCGGTTCC
           E  F  V     E  N  S     E     C  I  Q     C  H  P     E  C  L     P     Q  A  M
     2821 GAGTTTGTGG AGAACTCTGA GTGCATACAG TGCCACCCAG AGTGCCTGCC TCAGGCCATG
          CTCAAACACC TCTTGAGACT CACGTATGTC ACGGTGGGTC TCACGGACGG AGTCCGGTAC
           N  I  T     C  T  G  R     G  P  D     N  C  I  Q     C  A  H     Y  I  D
     2881 AACATCACCT GCACAGGACG GGGACCAGAC AACTGTATCC AGTGTGCCCA CTACATTGAC
          TTGTAGTGGA CGTGTCCTGC CCCTGGTCTG TTGACATAGG TCACACGGGT GATGTAACTG
           G  P  H     C  V  K  T     C  P  A     G  V  M  G     E  N  N     T  L  V
     2941 GGCCCCCACT GCGTCAAGAC CTGCCCGGCA GGAGTCATGG GAGAAAACAA CACCCTGGTC
          CCGGGGGTGA CGCAGTTCTG GACGGGCCGT CCTCAGTACC CTCTTTTGTT GTGGGACCAG
           W  K  Y     A  D  A  G     H  V  C     H  L  C     P  N  C     T  Y  G
     3001 TGGAAGTACG CAGACGCCGG CCATGTGTGC CACCTGTGCC ATCCAAACTG CACCTACGGA
          ACCTTCATGC GTCTGCGGCC GGTACACACG GTGGACACGG TAGGTTTGAC GTGGATGCCT
           C  T  G     P  G  L  E     G  C  P     T  N  G     P  K  I     P     S  I  A
     3061 TGCACTGGGC CAGGTCTTGA AGGCTGTCCA ACGAATGGGC CTAAGATCCC GTCCATCGCC
          ACGTGACCCG GTCCAGAACT TCCGACAGGT TGCTTACCCG GATTCTAGGG CAGGTAGCGG
           T  G  M     V  G  A     L  L  L     L  V  V     A  L  G     I     G  L  F
     3121 ACTGGGATGG TGGGGGCCCT CCTCTTGCTG CTGGTGGTGG CCCTGGGGAT CGGCCTCTTC
          TGACCCTACC ACCCCCGGGA GGAGAACGAC GACCACCACC GGGACCCCTA GCCGGAGAAG
           M  *
     3181 ATGTGA
          TACACT
```

TRUNCATED EPIDERIMAL GROWTH FACTOR RECEPTOR (EGFRT) FOR TRANSDUCED T CELL SELECTION

PRIORITY CLAIM

This application is a continuation of U.S. patent application Ser. No. 15/431,248, filed Feb. 13, 2017, which is a divisional of U.S. application Ser. No. 14/340,512, filed Jul. 24, 2014, issued as U.S. Pat. No. 9,580,685, which is a divisional of U.S. application Ser. No. 13/463,247, filed May 3, 2012, issued as U.S. Pat. No. 8,802,374, which is a continuation of International Application No. PCT/US2010/055329, filed Nov. 3, 2010, which claims the benefit of U.S. Provisional Application No. 61/257,567, filed Nov. 3, 2009, the subject matter of which is incorporated by reference as if fully set forth herein.

TECHNICAL FIELD

The present products and methods relate to the fields of immunology and purification of genetically modified cells, specifically to a truncated or otherwise modified receptor paired with a corresponding antibody, such as a polypeptide derived from human epidermal growth factor receptor (EGFR) paired with cetuximab, for use in cancer immunotherapy.

BACKGROUND

Immune cell products with homogenous expression of tumor targeting chimeric antigen receptors (CARs) are desirable for clinical evaluation of adoptive therapy strategies to eliminate the product-to-product variability of transgene expression otherwise intrinsic to transduction and other genetic modification procedures without subsequent selection. Immunotherapy using genetically redirected immune cells is an attractive approach for treating minimal residual disease in a variety of cancer patients. However, immunologic rejection of cell products expressing antibiotic selection proteins as part of the transduction strategy has impeded this strategy. A novel selection marker that is not expressed on human lymphocytes, does not contain endogenous signaling or trafficking function, and is recognized by a known, preferably commercially available, pharmaceutical grade antibody reagent that can be utilized for selection, in vivo tracking, and depletion of transduced cells would be a significant improvement in the art.

SUMMARY

Products and methods for purification, both in vivo and ex vivo, of genetically modified cells are provided herein. The genetically modified cells may be modified by transduction, or any other process that adds, deletes, alters, or disrupts an endogenous nucleotide sequence. The genetically modified cells may be transduced T cells with altered activity, including altered immunoactivity.

According to the embodiments described herein, a non-immunogenic selection epitope compatible with immunomagnetic selection facilitates immunotherapy in cancer patients without undesirable immunologic rejection of cell products (i.e. as seen when expressing antibiotic selection proteins) may be generated by removing certain amino acid sequences of the protein. In some embodiments, the non-immunogenic selection epitope is a gene encoding an endogenous cell-surface molecule that is modified or truncated to retain an extracellular epitope recognized by a known antibody or functional fragment thereof, and to remove any signaling or trafficking domains and/or any extracellular domains unrecognized by the known antibody. The removal of the signaling or trafficking domains and/or any extracellular domains unrecognized by the known antibody renders the endogenous cell-surface molecule inert, which is a desired property for the molecule. The non-immunogenic selection epitope may also be used for as a selection tool or tracking marker.

The modified endogenous cell-surface molecule may be, but is not limited to, any cell-surface related receptor, ligand, glycoprotein, cell adhesion molecule, antigen, integrin or cluster of differentiation (CD) that is modified as described herein. In some embodiments, the modified endogenous cell-surface molecule is a truncated tyrosine kinase receptor. In one aspect, the truncated tyrosine kinase receptor is a member of the epidermal growth factor receptor family (e.g., ErbB1, ErbB2, ErbB3, ErbB4).

Epidermal growth factor receptor, also known as EGFR, ErbB1 and HER1, is a cell-surface receptor for members of the epidermal growth factor family of extracellular ligands. Alterations in EGFR activity have been implicated in certain cancers. In a first aspect, a gene encoding an EGFR polypeptide comprising human epidermal growth factor receptor (EGFR) that is constructed by removal of nucleic acid sequences that encode polypeptides including the membrane distal EGF-binding domain and the cytoplasmic signaling tail (a "truncated EGFR" or "EGFRt"), but retains the extracellular membrane proximal epitope recognized by an anti-EGFR antibody. Preferably, the antibody is a known, commercially available anti-EGFR monoclonal antibody, such as cetuximab, matuzumab, necitumumab or panitumumab.

Application of biotinylated-cetuximab to immunomagnetic selection in combination with anti-biotin microbeads successfully enriches T cells that have been lentivirally transduced with EGFRt-containing constructs from as low as 2% of the population to greater than 90% purity without observable toxicity to the cell preparation. Constitutive expression of this inert EGFRt molecule does not affect T cell phenotype or effector function as directed by the coordinately expressed chimeric antigen receptor (CAR), CD19R. Through flow cytometric analysis, EGFRt was successfully utilized as an in vivo tracking marker for T cell engraftment in mice. Furthermore, EGFRt was demonstrated to have suicide gene potential through Erbitux® mediated antibody dependent cellular cytotoxicity (ADCC) pathways. Thus, EGFRt may be used as a non-immunogenic selection tool, tracking marker, and suicide gene for transduced T cells that have immunotherapeutic potential. The EGFRt nucleic acid may also be detected by means well known in the art.

In another embodiment, methods of discovering and designing modified, truncated or altered endogenous cell-surface molecules which bind to antibodies, preferably commercially available antibodies, as described herein are provided. The methods include modeling the protein of interest and truncating functional portions, while leaving the antibody-binding portions intact. The resulting modified receptor or ligand can be sorted using a labeled antibody and then enriched such that the concentration of the modified receptor or ligand is increased.

Yet another embodiment provides a method of selecting transduced T cells comprising transducing T cells with a modified, truncated or altered endogenous cell-surface molecule gene sequence (e.g., truncated EGFR) and then applying an antibody that binds the modified ligand or receptor sequence to the transduced T cells. If the modified receptor sequence is EGFRt, the antibody is preferably a biotinylated anti-EGFR monoclonal antibody. The T cells are then sorted by adding anti-biotin microbeads and selecting the T cells using immunomagnetic separation, adding fluorochrome-conjugated anti-biotin and selecting the T cells using Fluorescence Activated Cell Sorting, or any other reliable method of sorting the cells. The modified ligand or receptor sequences, such as the EGFRt sequence, may be contained in a suitable transfer vehicle such as a lentiviral vector.

These and other embodiments are further explained in the drawing and detailed description herein.

BRIEF DESCRIPTION OF THE DRAWINGS

FIG. 2a is a schematic of the cetuximab biotinylation and reformulation process. FIG. 2b is a graph showing titration of biotinylated cetuximab. $10^6$ EGFR+ cells were stained with either 0 µg (black), 1.45 µg (red), 0.145 µg (orange), 14.5 ng (yellow), 1.45 ng (green), 0.145 ng (blue) or 14.5 µg (purple) of biotinylated cetuximab followed by 0.5 □µg PE-conjugated streptavidin and analyzed by flow cytometry. 14.5 ng or more of biotinylated cetuximab was deemed sufficient for future staining. FIG. 2c depicts schematics of both the immunomagnetic (top) and the fluorescence activated cell sorting (bottom) EGFRt selection procedures.

FIG. 2d shows immunomagnetic selection of various T cell lines lentivirally transduced with CAR and EGFRt containing constructs. Schematics of the CD19CAR-T2A-EGFRt (left) and CD19CAR-T2A-EGFRt-IMPDH2dm (right) constructs contained in lentiviral vectors are shown above the corresponding pre- and post-selection flow cytometric analyses for surface EGFRt expression. Codon optimized sequence portions of the CD19-specific, CD28 co-stimulatory CAR, followed by the self-cleavable T2A, EGFRt and IMPDH2dm selection markers are indicated, along with the Elongation Factor 1 promoter sequences (EF-1p), and the GCSFR alpha chain signal sequences (GCSFRss, which directs surface expression). Flow cytometric analysis of lentivirally transduced T cell lines that had been stained with a biotinylated-cetuximab antibody and PE-conjugated anti-biotin antibody (black histograms) was performed on both the input T cells (PRE SLXN) and the positive fraction obtained from AutoMACS™ (POS FRXN). Open histograms represent staining with PE-conjugated anti-biotin antibody alone, and the percent positive cells are indicated in each histogram. Selection of CD19CAR+EGFRt+ Line A occurred 3 days after transduction of T cell blasts. Selection of CD19CAR+EGFRt+ Line B occurred after 3 REM stimulations of transduced CMVpp65-specific $T_{CM}$-derived cells. Selection of CD19CAR+EGFRt+ Line C occurred after 2 REM stimulations of transduced CD8+ $T_{CM}$-derived cells. Selection of CD19CAR+EGFRt+ Line D occurred after 1 REM stimulation of transduced $T_{EM}$-derived cells. Selection of CD19CAR+EGFRt+IMPDH2dm+ Line E occurred after 1 REM stimulation of transduced $T_{CM}$-derived cells.

In FIG. 3a, EGFRt expressed on T cells is not phosphorylated upon co-incubation with EGF. Negative control T cells, CD19CAR+EGFRt+ Line A cells, or A431 cells were incubated for 5 minutes with or without either 100 ng/mL EGF or cetuximab (referred to in the figure as Erbtx) and then lysed in the presence of phosphatase inhibitor. Lysates run on Western blots were then probed using antibodies specific for either β-actin, the cytoplasmic domain of EGFR, or the phosphorylated tyrosine at position 1068 of EGFR. FIG. 3b shows that EGF does not bind to the surface of EGFRt expressing T cells. A431, Line A, and negative control T cells were stained with PE-conjugated anti-EGFR, or either biotinylated cetuximab or biotinylated EGF followed by PE-conjugated streptavidin (black histogram) versus PE-conjugated isotype control Ab or streptavidin alone (open histogram) by flow cytometry. Percent positive staining is indicated in each histogram.

FIG. 4a is a line graph showing expansion of EGFRt-selected T cells, Lines A-E, over 12 or more days after rapid expansion medium (REM) stimulation was initiated on the day of AutoMACS™ selection (day 0). (MACS is magnetic activated cell sorting.) Expansion of T cells in rapid expansion medium (REM) involved the incubation of $10^6$ T cells with 30 ng/mL anti-$CD3_\epsilon$ (OKT3; Ortho Biotech, Raritan, N.J.), $5\times10^7$ 7-irradiated PBMCs (3500 cGy), and $10^7$ γ-irradiated LCLs (8000 cGy) in 50 mL CM; with addition of 50 U/mL rhIL-2 and 10 ng/ml rhIL-15 (CellGenix) every 48 hours, beginning on day 1. T cells were re-stimulated in this manner every 14 days. FIG. 4b shows histograms representing EGFRt-selected T cells (11 to 13 days after stimulation) that were phenotyped for surface EGFR (i.e., EGFRt, with biotinylated cetuximab), Fc (i.e., CAR), and T cell markers CD4 or CD8, (black histogram) vs. isotype control Ab (open histogram) by flow cytometry. Percent positive staining is indicated in each histogram. "N.D." indicates no data. FIG. 4C are five lines graphs, one for each of Lines A-E, of EGFRt-selected T cells (within 11 to 15 days after REM stimulation) incubated for 4 hours with $^{51}$Cr-labeled NSO, U251T, CD19t-expressing NSO, CMV pp65-expressing U251T, CD19-expressing Daudi or SupB15, or OKT3-expressing LCL cells as targets at the indicated E:T ratios. Chromium release was measured to determine cytotoxic activity. FIG. 4d is a graph showing MPA resistance of the CD19CAR+EGFRt+IMPDH2dm+ Line E. Control T cells that do not express IMPDH2dm and EGFRt-selected IMPDH2dm-expressing Line E cells were cultured either with or without 1 µM MPA and total cell numbers were monitored.

FIG. 7 is the nucleotide (sense strand is SEQ ID NO: 1, antisense strand is SEQ ID NO: 2) and amino acid (SEQ ID NO: 3) sequences of GMCSFR alpha chain signal sequence linked to EGFRt. The GMCSFR alpha chain signal sequence, which directs surface expression, is encoded by nucleotides 1-66. EGFRt is encoded by nucleotides 67-1071.

FIG. 8 is the nucleotide (sense strand is SEQ ID NO: 4, antisense strand is SEQ ID NO: 5) and amino acid (SEQ ID NO: 6) sequences of CD19R-CD28gg-Zeta(CO)-T2A-EG-FRt. CD19R-CD28gg-Zeta(CO) is encoded by nucleotides 1-2040; T2A is encoded by nucleotides 2041-2112; GMCSFR is encoded by nucleotides 2113-2178; EGFRt is encoded by nucleotides 2179-3186.

DETAILED DESCRIPTION

Figure 1:
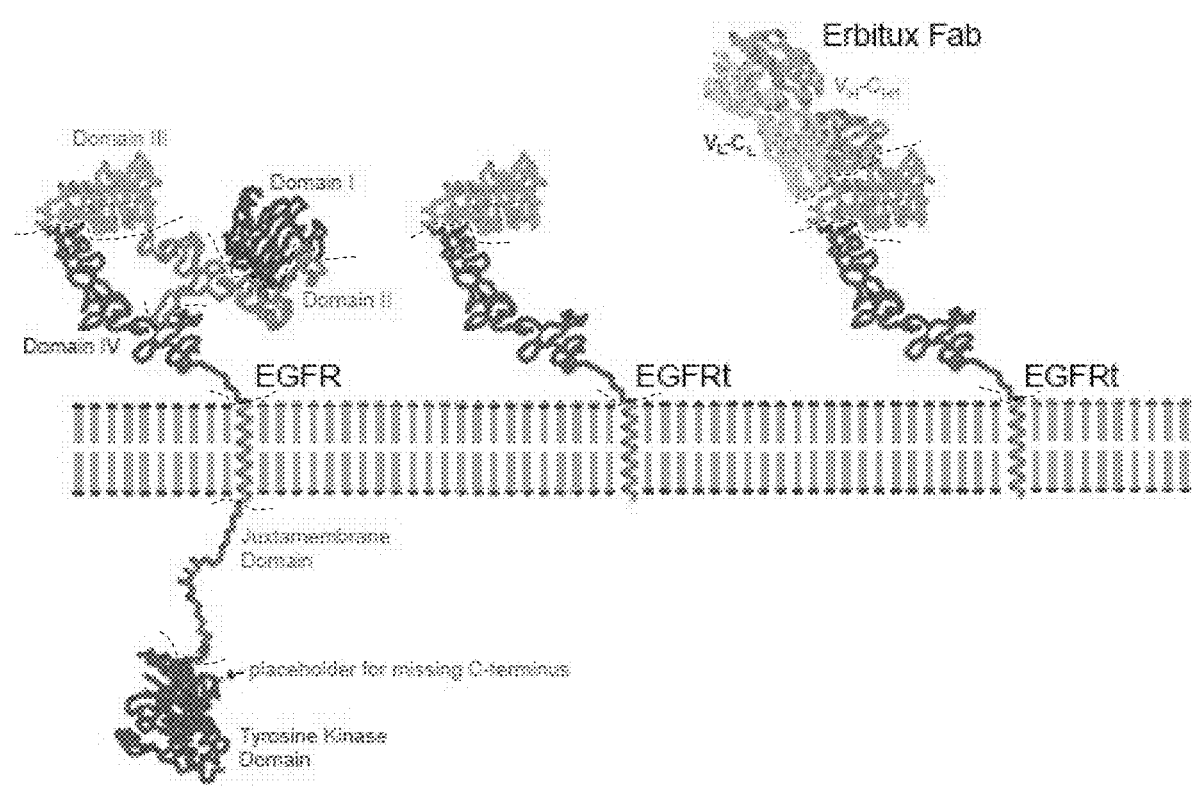
FIG. 1 is a molecular model of EGFR vs. EGFRt proteins based on the crystal structure files. The EGFR structure on the left shows a full-length EGFR with the structure of the four extracellular domains (Domains I-IV). The middle structure shows the truncated EGFR (EGFRt), which is missing Domain I, Domain II, the Juxatmembrane Domain, and the Tyrosine Kinase Domain as compared to an unmodified EGFR. The EGFRt on the right shows truncated structure bound to Eribitux® Fab, comprised of $V_H$-$C_{H1}$ and $V_L$-$C_L$. The domains are separated with dotted lines.

Certain embodiments of the invention are described in detail, using specific examples, sequences, and drawings. The enumerated embodiments are not intended to limit the invention to those embodiments, as the invention is intended to cover all alternatives, modifications, and equivalents, which may be included within the scope of the present invention as defined by the claims. One skilled in the art will recognize many methods and materials similar or equivalent to those described herein, which could be used in the practice of the present invention.

Erbitux® is a registered trademark for the anti-EGFR monoclonal antibody cetuximab and is intended to independently include the trade name product formulation, the generic drug, and the active pharmaceutical ingredient(s) of the trade name product.

The term "genetic modification" means any process that adds, deletes, alters, or disrupts an endogenous nucleotide sequence and includes, but is not limited to viral mediated gene transfer, liposome mediated transfer, transformation, transfection and transduction, e.g., viral mediated gene transfer such as the use of vectors based on DNA viruses such as lentivirus, adenovirus, retroviruses, adeno-associated virus and herpes virus.

The term "antibody" includes monoclonal antibodies, polyclonal antibodies, dimers, multimers, multispecific antibodies and antibody fragments that may be human, mouse, humanized, chimeric, or derived from another species. A "monoclonal antibody" is an antibody obtained from a population of substantially homogeneous antibodies that is being directed against a specific antigenic site.

"Variant" refers to polypeptides having amino acid sequences that differ to some extent from a native sequence polypeptide. Ordinarily, amino acid sequence variants will possess at least about 80% sequence identity, more preferably, at least about 90% homologous by sequence. The amino acid sequence variants may possess substitutions, deletions, and/or insertions at certain positions within the reference amino acid sequence.

"Percentage identity" or "percent identity" is defined as the percentage of residues in the amino acid sequence variant that are identical after best aligning the sequences and introducing gaps, if necessary, to achieve the maximum percent sequence identity. Methods and computer programs for the alignment are well known in the art. Such programs include GAP, BESTFIT, FASTA, BLAST or Align 2.

"Antibody-dependent cell-mediated cytotoxicity" and "ADCC" refer to a cell-mediated reaction in which nonspecific cytotoxic cells that express Fc receptors, such as natural killer cells, neutrophils, and macrophages, recognize bound antibody on a target cell and cause lysis of the target cell. ADCC activity may be assessed using methods, such as those described in U.S. Pat. No. 5,821,337.

"Effector cells" are leukocytes which express one or more constant region receptors and perform effector functions.

To "treat" a disease or a disorder, such as cancer, means to take either therapeutic measures or preventative measures to lessen or abate the disease or disorder. Such treatment includes prevention, alleviation of symptoms, diminishment or stabilization of scope, and/or remission.

The term "therapeutically effective amount" refers to an amount of a compound or molecule effective to treat a disease or disorder.

"Cancer" refers to cells undergoing uncontrolled cellular growth. Examples of cancer include colorectal cancer and head and neck cancer. A "chemotherapeutic agent" is a chemical compound useful in the treatment of cancer.

A "cytokine" is a protein released by one cell to act on another cell as an intercellular mediator.

"Non-immunogenic" refers to a material that does not initiate, provoke or enhance an immune response where the immune response includes the adaptive and/or innate immune responses.

The term "gene" means the segment of DNA involved in producing a polypeptide chain; it includes regions preceding and following the coding region "leader and trailer" as well as intervening sequences (introns) between individual coding segments (exons). Some genes may be developed which lack, in whole or in part, introns. Some leader sequences may enhance translation of the nucleic acid into polypeptides.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, a "vector" may be any agent capable of delivering or maintaining nucleic acid in a host cell, and includes viral vectors (e.g. retroviral vectors, lentiviral vectors, adenoviral vectors, or adeno-associated viral vectors), plasmids, naked nucleic acids, nucleic acids complexed with polypeptide or other molecules and nucleic acids immobilized onto solid phase particles. The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art. Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

"Receptor" means a polypeptide that is capable of specific binding to a molecule. Whereas many receptors may typically operate on the surface of a cell, some receptors may bind ligands when located inside the cell (and prior to transport to the surface) or may reside predominantly intracellularly and bind ligand therein.

"Antibody or functional fragment thereof" means an immunoglobulin molecule that specifically binds to, or is immunologically reactive with a particular antigen or epitope, and includes both polyclonal and monoclonal antibodies. The term antibody includes genetically engineered or otherwise modified forms of immunoglobulins, such as intrabodies, peptibodies, chimeric antibodies, fully human antibodies, humanized antibodies, and heteroconjugate antibodies (e.g., bispecific antibodies, diabodies, triabodies, and tetrabodies). The term functional antibody fragment includes antigen binding fragments of antibodies, including e.g., Fab', F(ab').sub.2, Fab, Fv, rIgG, and scFv fragments. The term scFv refers to a single chain Fv antibody in which the variable domains of the heavy chain and of the light chain of a traditional two chain antibody have been joined to form one chain.

In one embodiment, a gene encoding a modified endogenous cell-surface molecule that may be used as a non-immunogenic selection epitope compatible with immunomagnetic selection is provided. Such a non-immunogenic selection epitope may facilitate immunotherapy in cancer patients without undesirable immunologic rejection of cell products. The endogenous cell surface molecule may be modified or truncated to retain an extracellular epitope recognized by a known antibody or functional fragment thereof, and to remove any signaling or trafficking domains and/or any extracellular domains unrecognized by said known antibody. A modified endogenous cell surface molecule which lacks a signaling or trafficking domain and/or any extracellular domains unrecognized by said known antibody is rendered inert.

The modified endogenous cell-surface molecule may be, but is not limited to, any non-immunogenic cell-surface related receptor, glycoprotein, cell adhesion molecule, antigen, integrin or cluster of differentiation (CD) that is modified as described herein. Modification of such cell-surface molecules is accomplished by keeping an epitope that is recognized by a known antibody or functional fragment thereof; and removing any signaling or trafficking domains and/or any extracellular domains unrecognized by a known antibody. Removal of the signaling or trafficking domains and/or any extracellular domains unrecognized by a known antibody renders the endogenous cell-surface molecule non-immunogenic and/or inert.

Examples of endogenous cell-surface molecules that may be modified or truncated according to the embodiments described herein include, but are not limited to EpCAM, VEGFR, integrins (e.g., integrins αvβ3, α4, αIIbβ3, α4β7, α5β1, αvβ3, αv), TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, or clusters of differentiation (e.g., CD2, CD3, CD4, CD5, CD11, CD11a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7).

Corresponding commercial antibodies that may be used to recognize a modified or truncated endogenous cell-surface molecule include, but are not limited to, 3F8, abagovomab, abciximab, adecatumumab, afutuzumab, alemtuzumab, altumomab pentetate, anatumomab mafenatox, apolizumab, arcitumomab, aselizumab, atlizumab (=tocilizumab), basiliximab, bectumomab, benralizumab, besilesomab, bivatuzumab mertansine, blinatumomab, brentuximab vedotin, cantuzumab mertansine, capromab pendetide, catumaxomab, CC49, cedelizumab, celmoleukin, citatuzumab bogatox, clenoliximab, clivatuzumab tetraxetan, CNTO-95, conatumumab, dacetuzumab, daclizumab, daratumumab, detumomab, ecromeximab, edrecolomab, efalizumab, elotuzumab, enlimomab pegol, epitumomab cituxetan, epratuzumab, erlizumab, etaracizumab, fanolesomab, faralimomab, farletuzumab, galiximab, gavilimomab, gemtuzumab ozogamicin, glembatumumab vedotin, gomiliximab, ibalizumab, ibritumomab tiuxetan, igovomab, intetumumab, iratumumab, inolimomab, inotuzumab ozogamicin, ipilimumab, keliximab, labetuzumab, lintuzumab, lexatumumab, lucatumumab, lumiliximab, mapatumumab, maslimomab, milatuzumab, minretumomab, mitumomab, muromonab-CD3, naptumomab estafenatox, natalizumab, ocrelizumab, odulimomab, ofatumumab, olaratumab, oportuzumab monatox, oregovomab, otelixizumab, pemtumomab, priliximab, PRO 140, rituximab, rovelizumab, ruplizumab, satumomab pendetide, siplizumab, sontuzumab, tadocizumab, taplitumomab paptox, teneliximab, teplizumab, TGN1412, ticilimumab (=tremelimumab), tigatuzumab, tocilizumab (=atlizumab), toralizumab, tositumomab, tremelimumab, tucotuzumab, vedolizumab, veltuzumab, visilizumab, vitaxin, volociximab, votumumab, zanolimumab, ziralimumab, zolimomab aritox.

In some embodiments, the modified endogenous cell-surface molecule is encoded by a modified or truncated tyrosine kinase receptor gene. Examples of tyrosine kinase receptors that may be modified or truncated according to the embodiments described herein include, but are not limited to, members of the endothelial growth factor receptor family (EGRF/ErbB1/HER1; ErbB2/HER2/neu; ErbB3/HER3; ErbB4/HER4), hepatocyte growth factor receptor (HGFR/c-MET) and insulin-like growth factor receptor-1 (IGF-1R). According to some embodiments, modified tyrosine kinase receptors retain an extracellular epitope recognized by a known antibody or functional fragment thereof, and lack at least a tyrosine kinase domain. A modified tyrosine kinase receptor which lacks at least a tyrosine kinase domain renders the receptor inert.

Commercial antibodies that may be used to recognize a modified tyrosine kinase receptor include, but are not limited to AMG-102, AMG-479, BIIB022OA-5D5, CP-751, 871, IMC-A12, R1507, cetuximab, cixutumumab, ertumaxomab, figitumumab, matuzumab, necitumumab, panitumumab, pertuzumab, nimotuzumab, robatumumab, trastuzumab, zalutumumab.

In one embodiment, the modified endogenous cell surface molecule is a truncated EGFR (tEGFR) that lacks the membrane distal EGF-binding domain and the cytoplasmic signaling tail, but retains the extracellular membrane proximal epitope recognized by a known antibody or functional fragment thereof (e.g., cetuximab, matuzumab, necitumumab or panitumumab). In another embodiment, the tEGFR is missing Domain I, Domain II, the Juxtamembrane Domain and the Tyrosine Kinase Domain as compared to an unmodified EGFR (FIG. 1).

A gene encoding a modified endogenous cell surface molecule may be used as a cell selection or enrichment marker for a genetically modified population of immune cells (e.g., T cells). The gene encoding a modified endogenous cell surface molecule may be coupled to a gene encoding a tumor targeting chimeric antigen receptor (CAR). These genes may be inserted into a vector to transduce the population of T cells to be genetically modified. After transduction, the cells that are successfully transduced and express the CAR and modified endogenous cell-surface molecule are enriched by any suitable purification method, such as immunomagnetic purification with anti-biotin microbeads or fluorochrome-conjugated anti-biotin for fluorescence activated cell sorting, using a commercial antibody that recognizes the modified endogenous cell-surface molecule expressed by the transduced cell.

In another embodiment, a gene encoding a truncated human epidermal growth factor receptor (EGFRt) that lacks the membrane distal EGF-binding domain and the cytoplasmic signaling tail, but retains the extracellular membrane proximal epitope recognized by the FDA-approved anti-EGFR monoclonal antibody (mAb) cetuximab or another anti-EGFR antibody, is constructed and described herein. The EGFRt may be coupled with chimeric antigen receptors specific for a tumor associated antigen. The tumor associated antigen may be CD19, CD20, or CD22, or any other tumor associated antigen, but is preferably CD19 (CD19CAR). The tumor associated antigen is followed by a C-terminal 2A cleavable linker and the coding sequence for EGFRt. The biotinylated-cetuximab may be used in conjunction with commercially available anti-biotin microbeads for the purpose of immunomagnetic purification of the tumor associated antigen/CAR-expressing transductants. In the instance where the tumor associated antigen is CD19 the product is CD19CAR-expressing transductants. Alternatively, the biotinylated-cetuximab may be used in conjunction with Fluorochrome-conjugated anti-biotin for fluorescence activated cell sorting.

In another embodiment, a modified endogenous cell-surface molecule may be used as a marker for in vivo T cell engraftment. For example, when the modified endogenous cell-surface molecule is EGFRt, the EGFRt may be used to track the uptake of the T cells to which it is attached in vivo without affecting cellular function of the T cells or the cells to which the T cells are targeted, such as bone marrow cells in a transplant situation. The use of cetuximab conjugated to probes or reporter genes such as sr39TK may be used to improve the tracking potential of EGFRt-expressing cells to patients via PET imaging techniques.

In a separate embodiment, a modified endogenous cell-surface molecule may be used to induce cell suicide. For example, EGFRt may be used as a suicide gene via cetuximab mediated complement and/or antibody dependent cell mediated cytotoxicity (ADCC) pathways. The fact that cetuximab is a therapeutic FDA-approved antibody further facilitates the suicide gene potential of EGFRt in the clinical setting.

Figure 9:
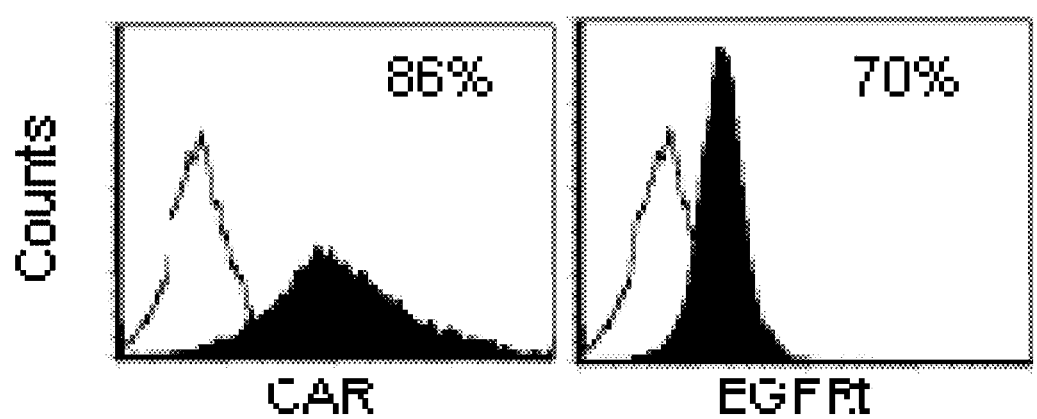
FIG. 9 is a graph showing CD19R-CD28gg-Zeta(CO)-T2A-EGFRt expression. Transduction of anti-CD3/anti-CD28 bead stimulated primary T cell blasts with the CD19R-CD28gg-Zeta(CO)-T2A-EGFRt_epHIV7 lentiviral vector (MOI=3) results in surface detection of both the CAR (using a biotinylated anti-Fc Ab and streptavidin-PE) and the truncated EGFR molecule (using a biotinylated cetuximab Ab and streptavidin-PE) by flow cytometry on day 4. The white peak in each panel is non-transduced control T cell blasts.

In other embodiments, the truncated epidermal growth factor receptor (EGFRt) selection epitope or other modified cell-surface molecule is attached to other sequences. One exemplar sequence is the GMCSFR alpha chain signal sequence, which directs surface expression, attached to EGFRt. GMCSFR is encoded by nucleotides 1-66 and EGFRt is encoded by nucleotides 67-1071 of SEQ ID NO: 1. See FIG. 7. Also in FIG. 7 is the antisense strand (SEQ ID NO: 2) and amino acid (SEQ ID NO: 3) sequences of GMCSFR alpha chain signal sequence linked to EGFRt. Another such sequence is a codon-optimized cDNA sequence encoding an anti-CD19 costimulatory chimeric antigen receptor (CD19R-CD28gg-Zeta(CO)), and a cleavable T2A linker. Cytotoxic T lymphocytes (CTLs) modified to express a CD19-specific chimeric antigen receptor (CAR) that signals via a cytoplasmic costimulatory (CD28) domain fused to the cytoplasmic CD3-domain exhibits superior anti-tumor potency that can be attributed to CD28-mediated survival and enhanced cytokine production. This construct may be further modified to incorporate a C-terminal 2A cleavable linker followed by the coding sequence for a truncated human EGFR (EGFRt) for the purpose of immunomagnetic purification of CAR-expressing transductants using cetuximab-biotin/anti-biotin microbeads. See the CD19R-CD28gg-Zeta(CO)-T2A-EGFRt sequence attached as FIG. 8, SEQ ID NOS: 4 (nucleotide sense strand), 5 (nucleotide anti-sense strand), and 6 (protein). Lentivector transduction of primary human T cells with this codon-optimized cDNA directs the coordinated expression of the CAR and EGFRt (FIG. 9).

To eliminate variability between transgene expression products otherwise intrinsic to transduction procedures without subsequent selection, a non-immunogenic selection epitope, EGFRt, compatible with immunomagnetic selection using the CliniMACS device (Miltenyi Biotec, Bergisch Gladbach, Germany) was developed. For example, EGFRt is a truncated human epidermal growth factor receptor that lacks the membrane distal EGF-binding domain and the ectoplasmic signaling tail, but retains the extracellular membrane proximal epitope recognized by the commercial anti-EGFR mAb cetuximab. See FIG. 1. Biotinylated-cetuximab is applied to immunomagnetic selection in combination with anti-biotin microbeads (Miltenyi). Human OKT3 blasts that had been lentivirally transduced with CD19R-CD28gg-Zeta (CO)-T2A-EGFRt were subjected to immunomagnetic selection using the Miltenyi AutoMACS device, and the frequency of EGFRt+CAR+ T cells was enriched from 22% (pre-selection) to 99% (post-selection) without observable toxicity to the cell preparation. It is also possible that, instead of or in addition to immunomagnetic sorting, the EGFRt can be purified using fluorescence-based cell sorting techniques.

Due to the absence of the EGF-binding domains and intracellular signaling domains, EGFRt is inactive when expressed by T cells. Importantly, the EGFRt-selected T cells maintain their desired effector phenotype—including anti-tumor cyotoxic activity mediated by the chimeric antigen receptor that is coordinately expressed with the EGFRt—and remain amenable to established expansion protocols.

Overall, this EGFRt has various advantages for immunotherapeutic cell products compared to other selection markers that have been previously reported. Specifically, unlike truncated CD4 and CD19, it is not endogenously expressed by subpopulations of lymphocytes. Furthermore, in contrast to truncated CD34 and low affinity nerve growth factor receptor, it does not have any activity that might negatively affect the immune cell product (i.e., in terms of signaling or trafficking). Lastly, it alone can be bound/recognized by a known, preferably commercially available, pharmaceutical grade antibody reagent, i.e., cetuximab. Together, these attributes make EGFRt a superior selection marker for any transfection/transduction system that can be applied to the generation of cell products for adoptive immunotherapy. Thus, EGFRt is well suited to be used as a selection marker for lentivirally transduced T cells of immunotherapeutic relevance.

Also provided are methods for identifying new therapeutic cell products having the following criteria: a modified endogenous cell-surface molecule, ligand or receptor that is not, as modified, endogenously expressed in the subject in which it is intended to be therapeutically utilized, does not have any immunoactivity or other functional activity that would hinder the functioning of the product or the subject into which the product is administered, and that it can be recognized by a known antibody.

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications.

Example 1: Generation of EGFRt and Immunomagnetic Selection of EGFRt Expressing T Cells Materials & Methods
Antibodies and Flow Cytometry FITC-, PE- and PerCP-conjugated isotype controls, PerCP-conjugated anti-CD8, FITC conjugated anti-CD4, PE-conjugated anti-IFNγ, PerCP-conjugated anti-CD45 and PE-conjugated streptavidin were obtained from BD Biosciences (San Jose, Calif.). Biotinylated anti-Fc was purchased from Jackson ImmunoResearch Laboratories, Inc. (Westgrove, Pa.). PE-conjugated anti-Biotin was purchased from Miltenyi Biotec (Auburn, Calif.). Biotinylated EGF was purchased from Molecular Probes® Invitrogen (Carlsbad, Calif.). PE-conjugated anti-EGFR was purchased from Abcam Inc. (Cambridge, Mass.). All antibodies and biotin-EGF were used according to the manufacturer's instructions. Flow cytometric data acquisition was performed on a FACScalibur (BD Biosciences), and the percentage of cells in a region of analysis was calculated using FCS Express V3 (De Novo Software, Los Angeles, Calif.).

For generation of the biotinylated-cetuximab, 200 mg of cetuximab (Erbitux®) was buffer exchanged (19 hours) to PBS (D-PBS, pH 7.5±0.1) using a MidGee Hoop Cartridge (UFP-30-E-H42LA) with 527 mL. The material at 2 mg/mL was then modified at a 20:1 ratio using Sulfo-NHS-LC-Biotin in a reaction that was carried out for 1 hour at room temperature and then diafiltered to remove the excess biotin. The 200 mg of biotinylated cetuximab was then buffer exchanged (18 hours) to PBS (D-PBS, pH 7.5±0.1) using MidGee Hoop Cartridge (UFP-30-E-H42LA) with 533 mL. Glycerol was added to a final concentration of 20% and then the material was frozen in vials.

Cell Lines

Unless otherwise indicated, all cell lines were maintained in RPMI 1640 (Irvine Scientific, Santa Ana, Calif.) supplemented with 2 mM L-glutamine (Irvine Scientific), 25 mM N-2-hydroxyethylpiperazine-N'-2-ethanesulfonic acid (HEPES, Irvine Scientific), 100 U/mL penicillin, 0.1 mg/mL streptomycin (Irvine Scientific), and 10% heat-inactivated fetal calf serum (FCS, Hyclone, Logan, Utah), hereafter referred to as culture media (CM).

To generate T cells, human peripheral blood mononuclear cells (PBMC) were isolated by density gradient centrifugation over Ficoll-Paque (Pharmacia Biotech, Piscataway, N.J.) from heparinized peripheral blood obtained from consented healthy donors participating on a City of Hope National Medical Center Internal Review Board-approved protocol. For generation of Line A, washed PBMC were stimulated with 25 U/mL IL-2 and a 1:1 (cell:bead) ratio of Dynabeads® Human T expander CD3/CD28 (Invitrogen, Carlsbad, Calif.). For generation of the other lines, washed PBMC were first autoMACS™ depleted using anti-CD45RA beads (Miltenyi Biotec) per the manufacturer's protocol, and in some cases also depleted with PE-conjugated anti-CD4 (BD Biosciences) with anti-PE beads (Miltenyi Biotec). The resulting cells then underwent autoMACS™ positive selection using biotinylated DREG56 (anti-CD62L) and anti-biotin beads (Miltenyi Biotec) to produce purified CD62L+CD45RO+ $T_{CM}$. CD8+ cells were further selected in some cases using AutoMACS™ (Miltenyi Biotec) per the manufacturer's protocol. CMV-specific cells were generated by stimulating T cells with 5 U/ml rhIL-2 (Chiron, Emeryville, Calif.) and autologous irradiated viral antigen presenting cells at a 4:1 (responder: stimulator) ratio once a week for three weeks, using 10% human serum instead of FCS to avoid non-specific stimulation. The viral antigen presenting cells were derived from PBMC that had been genetically modified to express CMVpp65 antigen.

PBMC were resuspended in nucleofection solution using the Human T cell Nucleofector kit (Amaxa Inc., Gaithersberg, Md.), and $5 \times 10^7$ cells were aliquoted into 0.2-cm cuvettes containing 10 μg HygroR-pp65_pEK (or pmaxGFP from Amaxa Inc., as a transfection control) in a final volume of 100 μL/cuvette, and electroporated using the Amaxa Nucleofector I (Amaxa Inc.), program U-14, after which cells were allowed to recover for 6 hours at 37° C. prior to γ-irradiation (1200 cGy).

The CD19CAR-T2A-EGFRt_epHIV7 (pJ02104) and CD19CAR-T2A-EGFRt-T2A-IMPDH2dm_epHIV7 (pJ02111) lentiviral constructs contain a) the chimeric antigen receptor (CAR) sequences consisting of the $V_H$ and $V_L$ gene segments of the CD19-specific FmC63 mAb, an IgG1 hinge-$C_{H2}$-$C_{H3}$, the transmembrane and cytoplasmic signaling domains of the costimulatory molecule CD28, and the cytoplasmic domain of the CD3ζ chain[10]; b) the self-cleaving T2A sequence[11]; c) the truncated EGFR sequence (See FIG. 1); and d) the IMPDH2 double mutant that confers MPA-resistance, as indicated. Lentiviral transduction was carried out on T cells that were stimulated with either 30 ng/mL anti-CD3$_\varepsilon$ (OKT3; Ortho Biotech, Raritan, N.J.) (i.e., for Line A) or human CD3/CD28Dynal beads ata 1:10 ratio (i.e., for Lines B, C, D and E) and 25 U IL2/ml. Cells were cultured for up to 2 hours at 37° C. on RetroNectin® (50 ug/ml) coated plates prior to addition of the lentivirus at an MOI of 3 and 5 μg/ml polybrene. After 4 hours, warm medium was added to triple to volume, and the cells were then washed and plated in fresh media after 48 hours. AutoMACS™ sorting of EGFRt-expressing cells was carried out with biotinylated cetuximab and anti-biotin microbeads (Miltenyi Biotec) as per the manufacturer's instructions. Expansion of T cells in rapid expansion medium (REM) involved the incubation of $10^6$ T cells with 30 ng/mL anti-CD3$_\varepsilon$ (OKT3; Ortho Biotech, Raritan, N.J.), $5 \times 10^7$ γ-irradiated PBMCs (3500 cGy), and $10^7$ γ-irradiated LCLs (8000 cGy) in 50 mL CM; with addition of 50 U/mL rhIL-2 and 10 ng/ml rhIL-15 (CellGenix) every 48 hours, beginning on day 1. T cells were re-stimulated in this manner every 14 days.

EBV-transformed lymphoblastoid cell lines (LCLs) were made from PBMC as previously described [13]. LCL-OKT3 cells were generated by resuspending LCL in nucleofection solution using the Amaxa Nucleofector kit T, adding OKT3-2A-Hygromycin_pEK (pJ01609) plasmid at 5 μg/$10^7$ cells, and electroporating cells using the Amaxa Nucleofector I, program T-20. The resulting LCL-OKT3-2A-Hygro_pEK (cJ03987) were grown in CM containing 0.4 mg/ml hygromycin. The mouse myeloma line NSO (gift from Andrew Raubitschek, City of Hope National Medical Center, Duarte, Calif.) was resuspended in nucleofection solution using the Nucleofector kit T (Amaxa Inc., Gaithersberg, Md.), CD19t-DHFRdm-2A-IL12_pEK (pJ01607) or GFP-IMPDH2dm-2A-IL15_pcDNA3.1(+) (pJ01043) plasmid was added at 5 μg/5×$10^6$ cells, and cells were electroporated using the Amaxa Nucleofector I, program T-27. The resulting NSO-CD19t-DHFRdm-2A-IL12_pEK (cJ03935) and NSO-GFP:IMPDH2-IL15(IL2ss)_pcDNA3.1(+) (cJ02096) were grown in DMEM (Irvine Scientific, Santa Ana, Calif.) supplemented with 10% heat-inactivated FCS, 25 mM HEPES, and 2 mM L-glutamine in the presence of either 0.05 uM methotrexate (MTX) or 6 μM mycophenolic acid (MPA). The tumorigenic strain of U251, termed U251T, was a kind gift of Dr. Waldemar Debinski (Wake Forest, N.C.). U251T-pp65 were generated by lentiviral transduction of U251T with pp65-2A-eGFP-ffluc_epHIV7 (pJ01928) at an MOI of 1. The resulting U251T-pp65-2A-eGFP-ffluc_e-pHIV7 were then FACS sorted for the GFP$^+$ population (cJ05058). The Daudi lymphoma line was purchased from ATCC and grown in media consisting of RPMI 1640 (Irvine Scientific), 2 mM L-Glutamine (Irvine Scientific), 10% heat-inactivated FCS (Hyclone). SupB15 acute lymphoblastic leukemia cells and A431 epidermoid carcinoma cells were purchased from ATCC.

Protein Analysis

Cells (up to $10^7$) were lysed with 80 μL of 1% Triton-X lysis buffer containing phosphatase inhibitor cocktail II (Sigma-Aldrich Corp., St. Louis, Mo.) (1:20 of inhibitor to buffer by volume). 50 μg of protein was loaded in each lane, and Western blots were probed with antibodies from the Phospho-EGF receptor antibody sampler kit (Cell Signaling Technology, Inc., Danvers, Mass.) followed by IRDye™ 680CW or 800CW conjugated goat anti-rabbit antibodies (LI-COR, Lincoln, Nebr.), as well as the IRDye™ 800 conjugated anti-beta-Actin antibody (LI-COR) as per the manufacturers' instructions. Blots were imaged on the Odyssey Infrared Imaging System (LI-COR).

Chromium-Release Assays

The cytolytic activity of T cells was determined by 4-hour chromium-release assay (CRA), where effector cells were seeded into triplicate wells of V-bottom 96-well micro-plates containing 5×$10^3$ $^{51}$Cr-labeled targeT cells (Na$_2^{51}$CrO$_4$; (5 mCi/m L); Amersham Pharmacia, Piscataway, N.J.) at various E:T ratios in 200 uL of CM and incubated for 4 hours at 5% CO2, 37° C. Plates were centrifuged, and 100 μl of supernatant was removed from each well to assess chromium release using a γ-counter (Packard Cobra II, Downer's Grove, Ill.). The percent specific lysis was calculated as follows: 100×(experimental release−spontaneous release)/ (maximum release−spontaneous release). Maximum release was determined by measuring the $^{51}$Cr content of wells containing labeled targets lysed with 2% SDS.

Antibody dependent cell mediated cytotoxicity was determined by chromium release as above using 5×$10^3$ $^{51}$Cr-labeled targeT cells that had been pre-incubated for 90 min with up to 10 μg/mL of either cetuximab or rituximab (a CD20-specific mAb), washed and then co-incubated with 5×$10^5$ freshly isolated PBMC.

T Cell Engraftment and Cetuximab Mediated Suicide In Vivo

For T cell engraftment, six- to ten-week old NOD/Scid IL-2RγC$^{null}$ mice are injected i.v. on day 0 with $10^7$ T cells (Line C). 2×$10^7$ irradiated (8000 rads) NSO-GFP:IMPDH2-IL15(IL2ss)_pcDNA3.1(+) (cJ02096) cells are administered i.p. 3 times a week starting on day 0 to provide a systemic supply of human IL-15 in vivo. Bone marrow was harvested from euthanized animals and analyzed by flow cytometry. Antibody dependent cell mediated cytotoxicity assays are performed to determine the activity of cetuximab against EGFRt$^+$ T cells.

Results

Immunomagnetic Selection of EGFRt Expressing T Cells

A truncated human EGFR (EGFRt), which contains only the transmembrane domain and extracellular domains III and IV of the full length EGFR, was generated as a non-immunogenic selection epitope compatible with immunomagnetic selection. As shown in the FIG. 1 molecular model, the EGFRt retains the ability to be bound by cetuximab, but not have any signaling capacity due to the absence of the intracellular domains. Furthermore, it lacks the N-terminal domain required for EGF-binding.

Figure 2A:
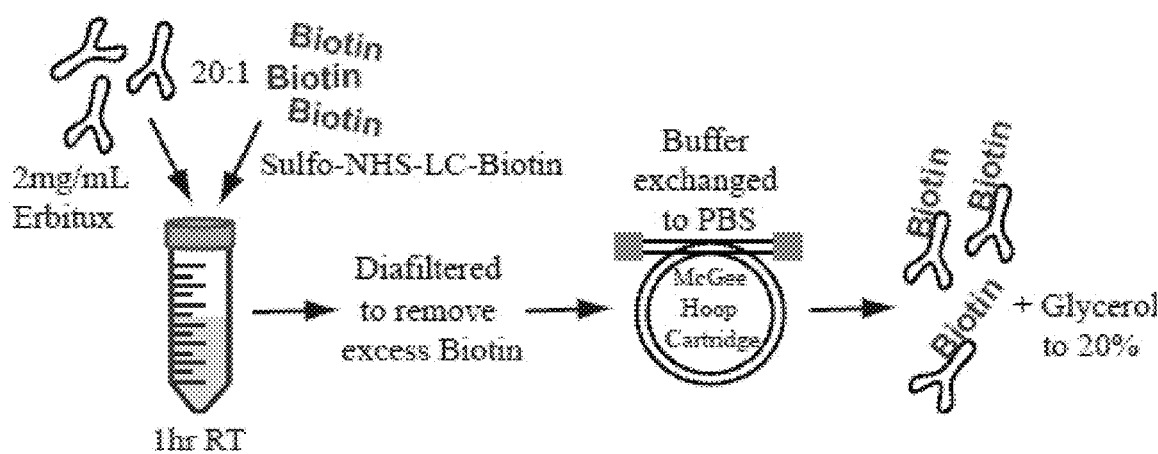
FIGS. 2a-d illustrate the selection of EGFRt+ T cells using biotinylated cetuximab (referred to in the figure as Erbitux®).
Figure 2B:
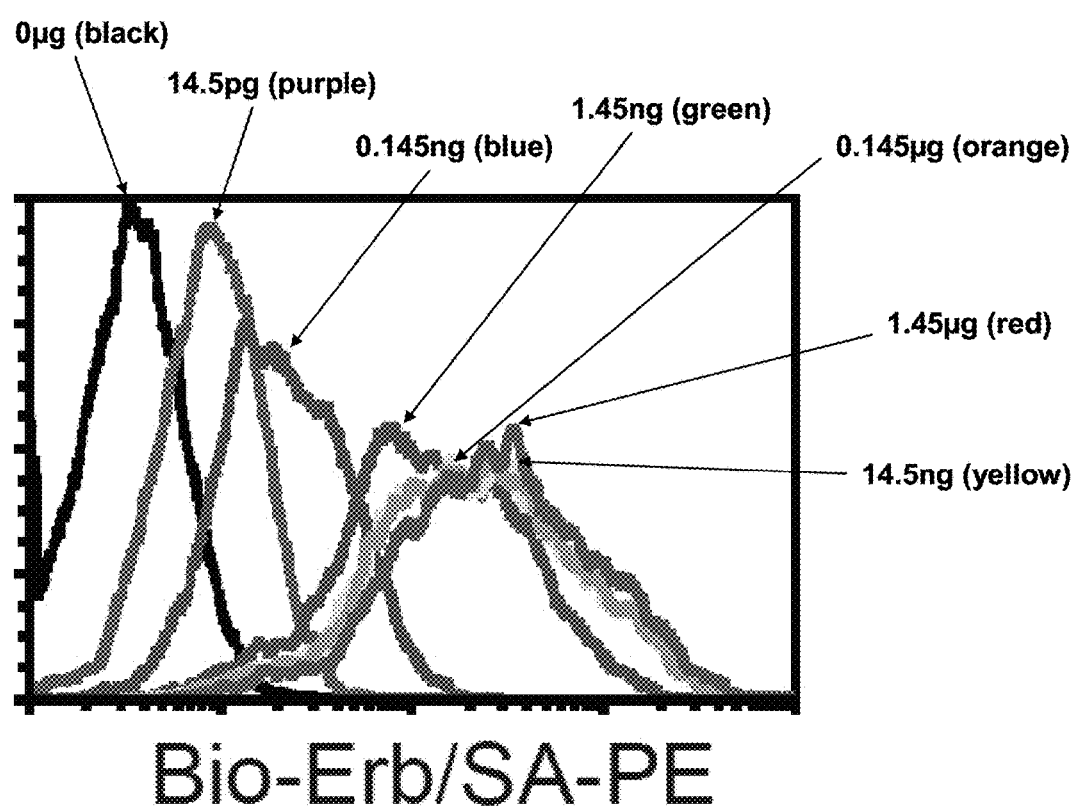
Figure 2C:
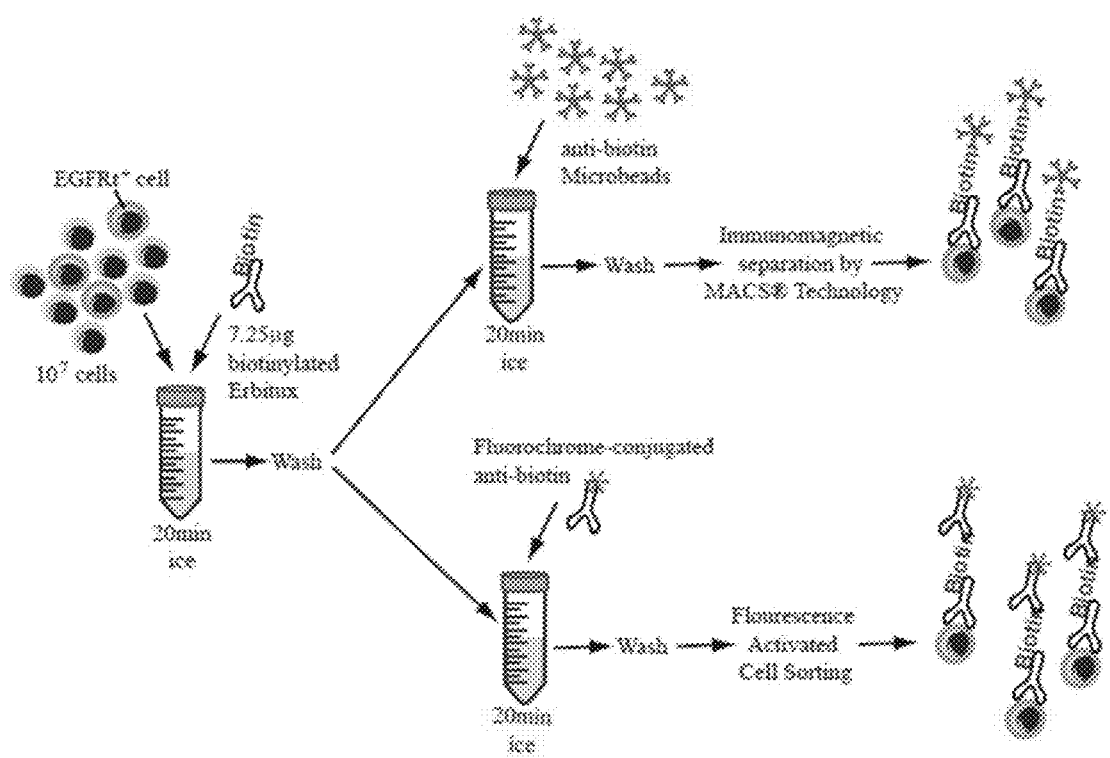
Figure 2D:
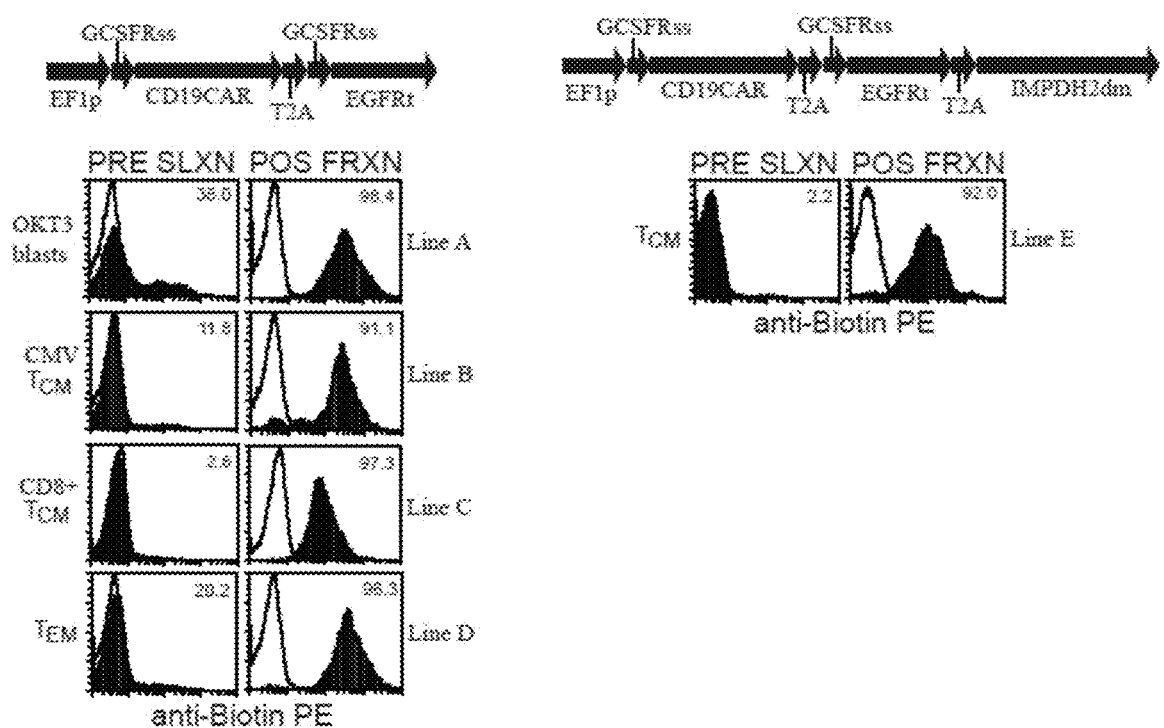

To immunomagnetically select for EGFRt-expressing cells, biotinylated-cetuximab was generated (FIG. 2a, b) to be used in conjunction with commercially available anti-biotin microbeads and an AutoMACS™ separator (Miltenyi Biotec) (FIG. 2c). Lentiviral transduction of various T cell lines with EGFRt-containing constructs, where the EGFRt gene was separated from other genes of interest on either one or both ends with the self-cleaving T2A sequence, consistently resulted in surface detection of the EGFRt molecule on less than 40% of the cells (FIG. 2d). Surface detection may also be accomplished with a EGFRt-sr39TK fusion. Immunomagnetic selection allowed for recovery of EGFRt$^+$ T cell populations with greater than 90% purity. T cell populations that underwent this transduction and selection procedure included anti-CD3/anti-CD28 bead stimulated T cell blasts (for Line A), central memory (CD45RO$^+$CD62L$^+$ T$_{CM}$) derived T cells (for Lines B, C and E), which in some cases were also pre-selected for CMV specificity (via the endogenous TCR; for Line B) or CD8 expression (for Line C), as well as effector memory (CD62L$^−$ CD45RO$^+$ T$_{EM}$) derived T cells (for line D). These data show that EGFRt can successfully be used as a selection marker for various sources of T cell transductants, even when the original transduction efficiency was as low a 2%.

Inactivity of EGFRt on Selected T Cells

Figure 3A:
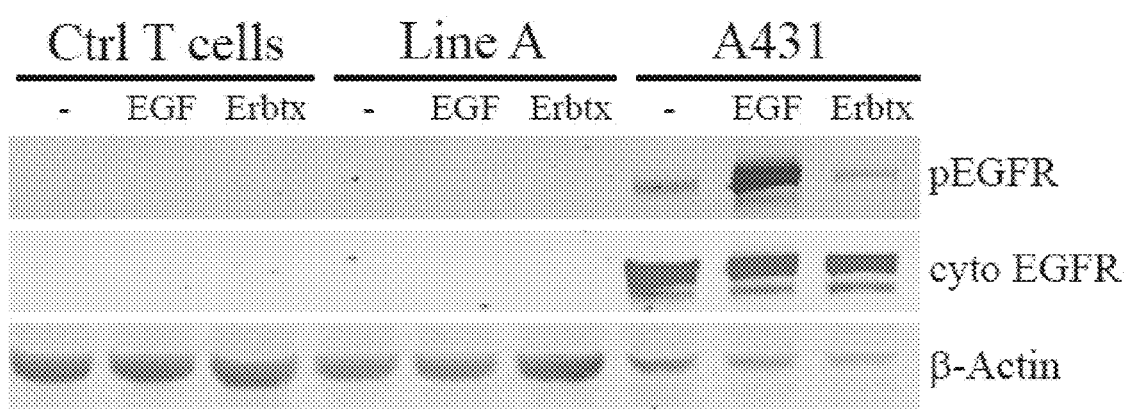
FIGS. 3a-b show that the EGFRt expressed on selected T cells is inert.
Figure 3B:
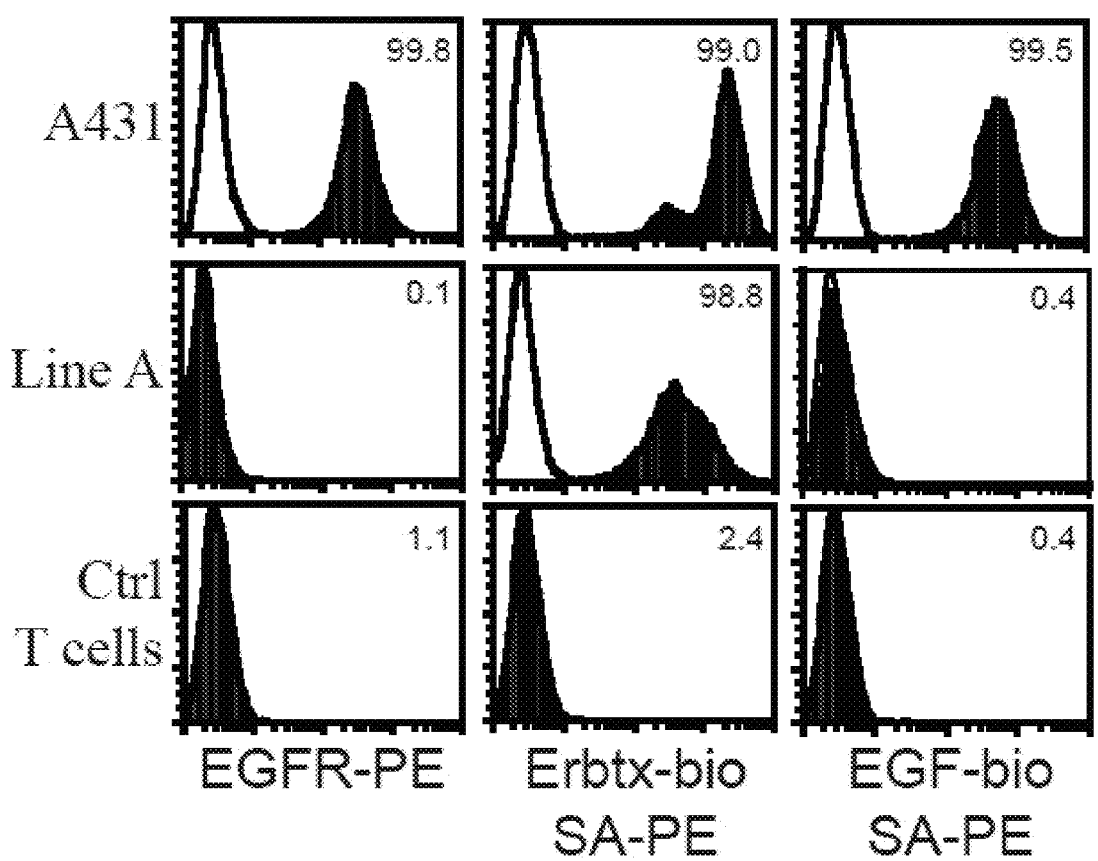

To confirm that the EGFRt is inactive, Western immunoblot analyses for EGFR phosphorylation were carried out on the EGFRt-selected T cells after culture with either EGF or cetuximab. As expected, cetuximab did not induce EGFR phosphorylation above background even in the EGFR$^+$ cell line A431 (FIG. 3a). Furthermore, in contrast to that seen with the A431 cells, no phosphorylation was seen in lysates of Line A after co-incubation with EGF. Indeed, using biotinylated EGF, flow cytometric analysis confirmed that EGF cannot bind the EGFRt-selected T cells (FIG. 3b), as expected due to the truncation in its N-terminus. These EGFRt$^+$ T cells were also not recognized by another anti-EGFR antibody distinct from cetuximab.

Maintenance of Effector Phenotype in Expanded EGFRt+ CD19CAR+ T Cells

Figure 4A:
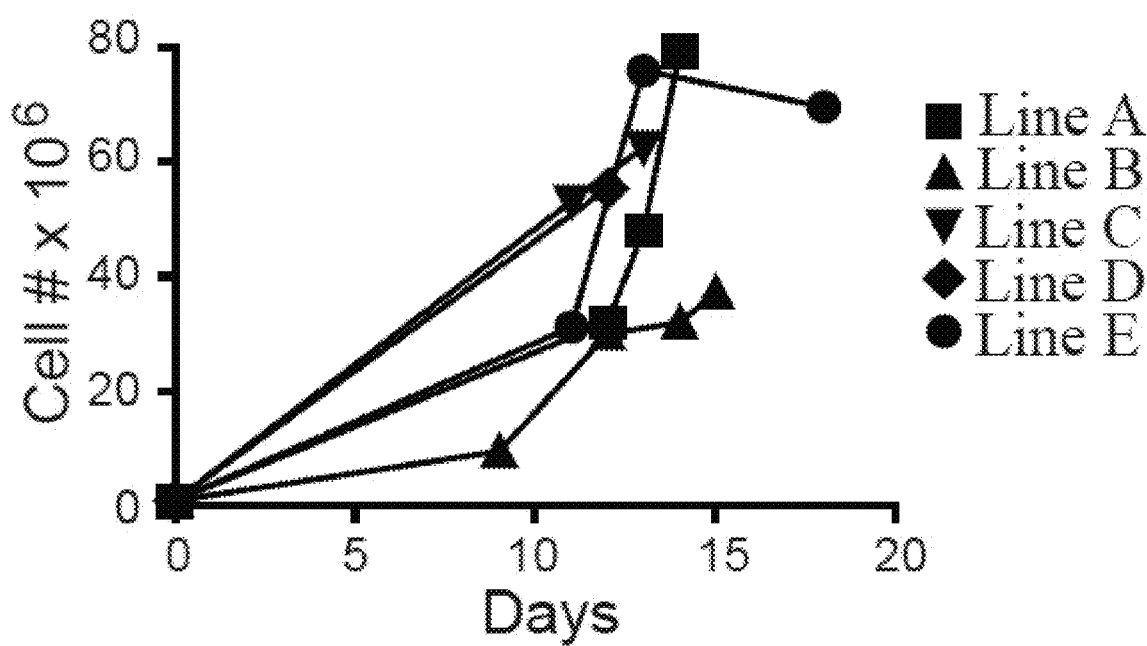
FIGS. 4a-d illustrate that selected EGFRt+ CD19R+ T cells can be expanded with maintenance of effector phenotype.
Figure 4B:
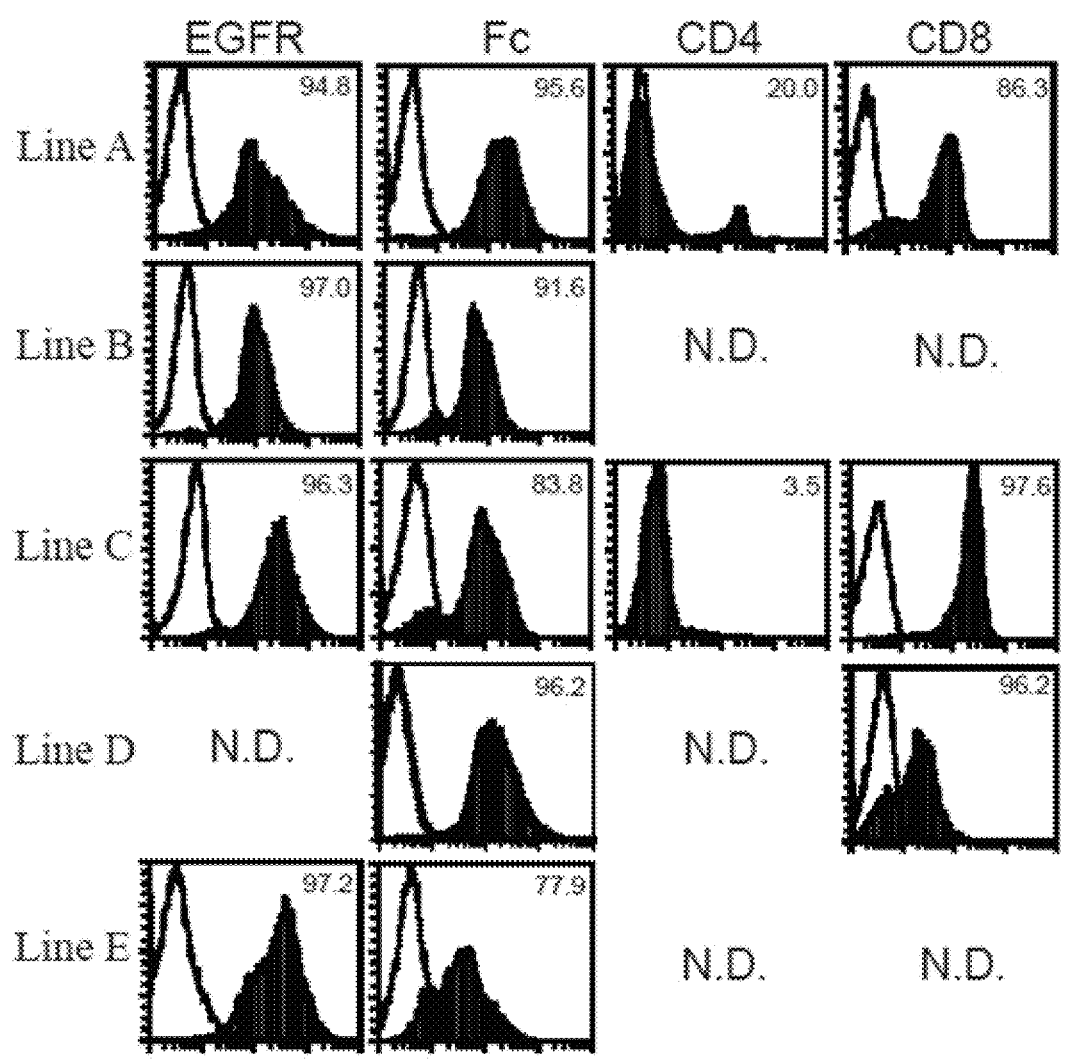
Figure 4C:
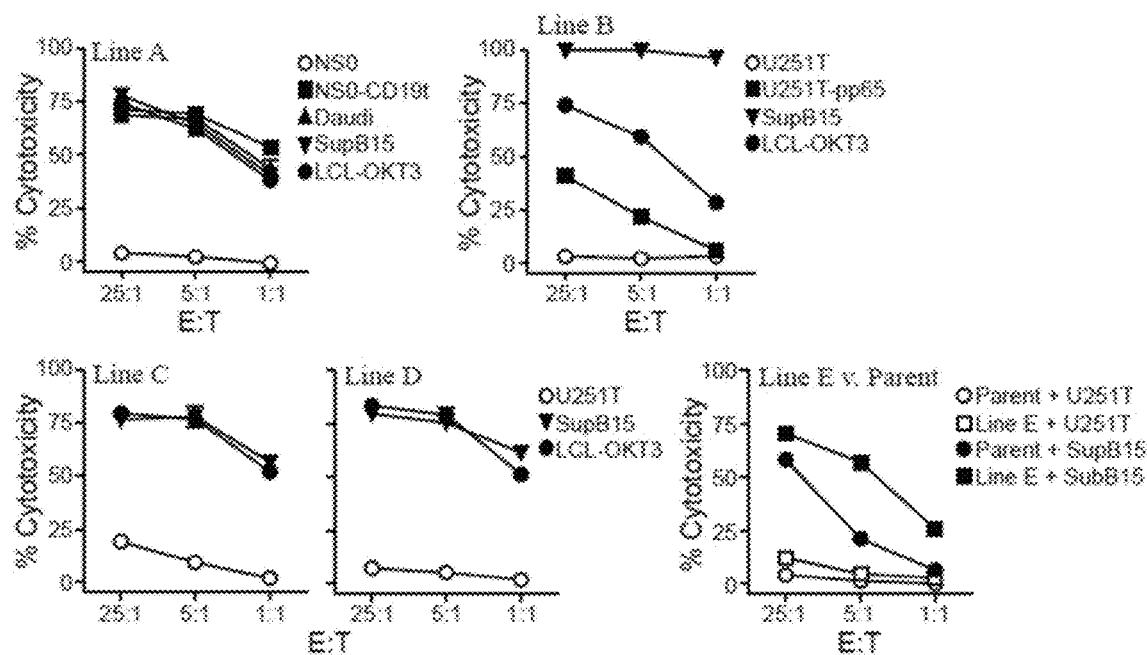

Directly after AutoMACS™ separation, the selected T cells were expanded 30-fold or greater within 12 days after REM stimulation with OKT3, irradiated PBMC feeders and LCL, IL-2 and IL-15 (FIG. 4a). Flow cytometric analysis of the resulting expanded EGFRt+ T cells further confirmed that that they express the CD19CAR and T cell markers such as CD8, TCR, CD3, perforin, granzyme, etc. (FIG. 4b). Furthermore, CD19CAR-directed cytotoxic activity of these EGFRt-selected lines is evident in chromium release assays using CD19-expressing tumor targets (FIG. 4c). A direct comparison of the CD19-specific reactivity of Line E versus its non-selected or 'parental' counterpart shows that there is enhanced CD19CAR-mediated cytotoxicity upon EGFRt-selection. In addition, the CMV-specific $T_{CM}$-derived CD19CAR+EGFRt+ Line B cells also show cytotoxic activity through their endogenous T cell receptor against targets expressing CMV-pp65 antigen.

Figure 4D:
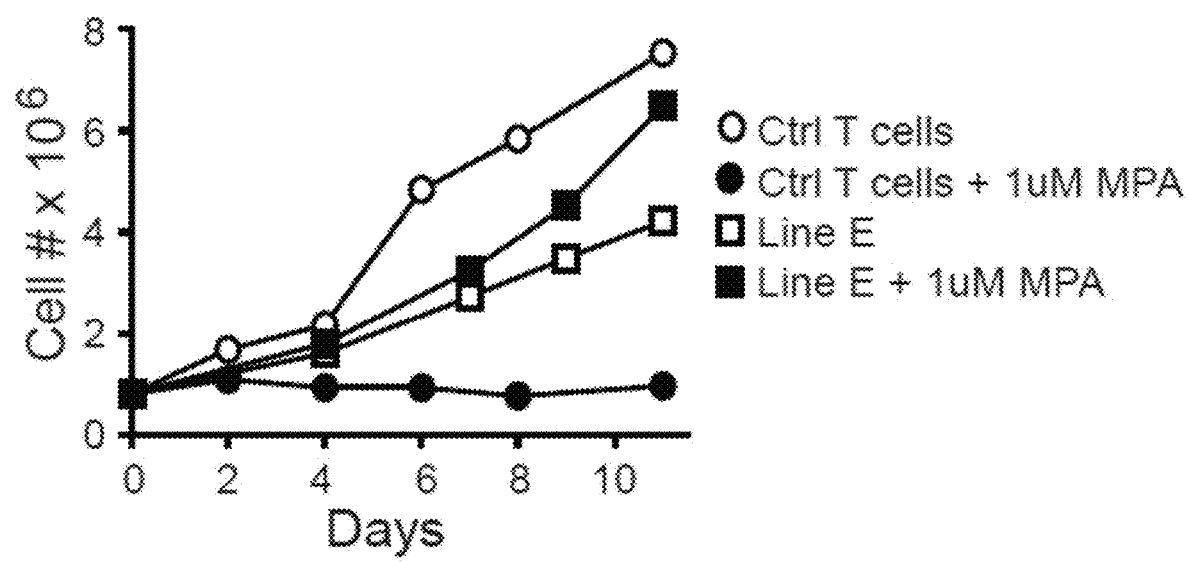

For the CD19CAR+EGFRt+ IMPDH2dm+ Line E, the ability of the inosine monophosphate dehydrogenase 2 double mutant (IMPDH2dm) to confer resistance to the IMPDH2-inhibitor mycophenolic acid (MPA; a common immunosuppressant used to prevent rejection in organ transplantation) was also tested. Upon culture in 1 uM MPA, the survival and/or proliferation of Line E cells is not inhibited (FIG. 4d). This is in contrast to the inhibition seen with a control T cell line that lacks expression of the IMPDH2dn gene. These data provide further evidence that EGFRt-mediated selection results in the corresponding selection of the other genes present in the lentiviral construct used to transduce T cells.

Tracking of EGFRt+ T Cells In Vivo

Figure 5:
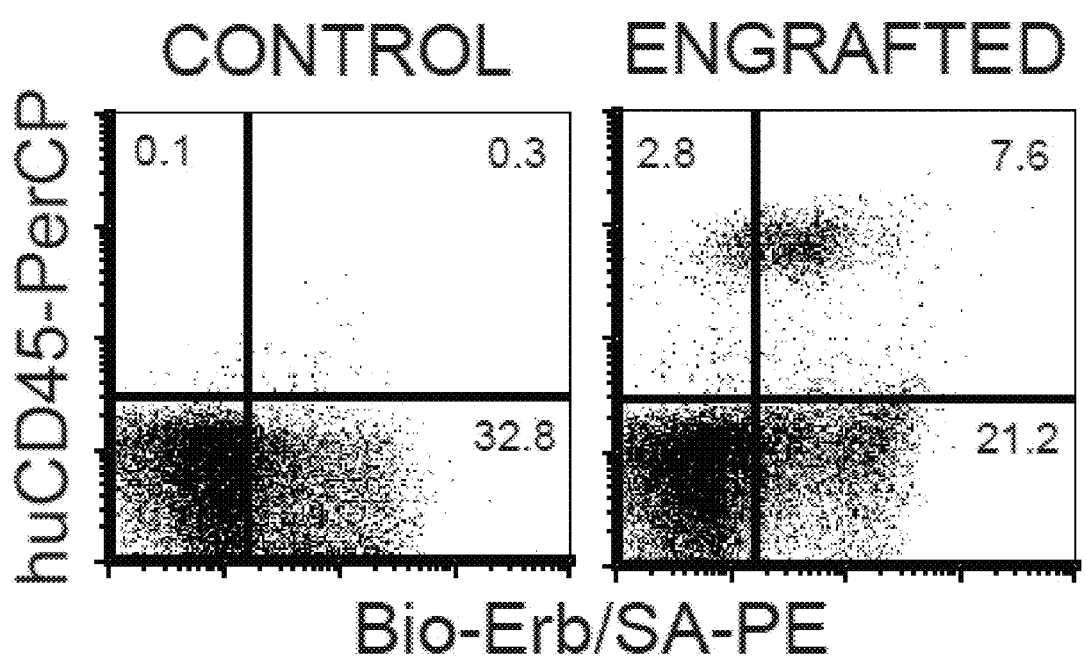
FIG. 5 shows EGFRt expression can be used as a tracking marker for in vivo T cell engraftment. Day 36 bone marrow harvested from a control mouse or from a mouse that had received $10^7$ CD19CAR+EGFRt+ Line C at day 0 was stained using PerCP-conjugated anti-human CD45 and biotinylated cetuximab ("Bio-Erb") followed by PE-conjugated streptavidin. Quadrants were created based on isotype control staining, and percent positive staining in each quadrant is indicated in each histogram.

To test the potential for detecting in vivo engrafted T cells, bone marrow cells collected from mice that had been engrafted with CD19CAR+EGFRt+ Line C was analyzed by flow cytometry using biotinylated cetuximab (FIG. 5). Control mice that did not receive T cells revealed that there was some cross-reaction of the cetuximab against murine EGFR. Thus, it was determined that successful detection of engrafted Line C cells required double staining for both human CD45 and EGFRt. Cells may also analyzed using immunohistochemistry to determine potential for screening biopsy material.

Cetuximab Mediated Cytotoxicity of EGFRt+ T Cells

Figure 6:
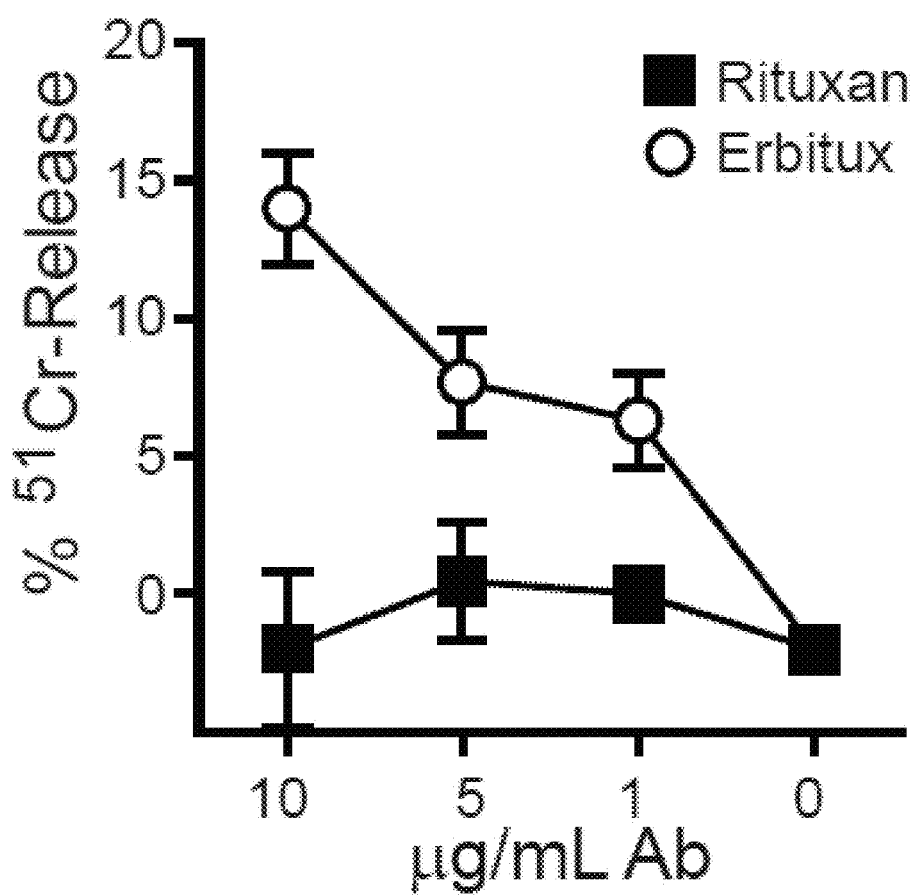
FIG. 6 is a graph showing EGFRt expression targets T cells for cetuximab (referred to in the figure as Erbitux®) mediated ADCC. $^{51}$Cr-labeled Line A cells were pre-incubated either with or without up to 20 µg/mL of cetuximab or the CD20-specific mAb Rituxan as a negative control prior to addition of human PBMC as effectors.

Because cetuximab is known to lyse EGFR-expressing cells via antibody dependent cell mediated cytotoxicity (ADCC), assays were performed to determine the ADCC activity of cetuximab against EGFRt+ T cells (FIG. 6). Using $^{51}$Cr-labeled Line A cells as targeted and freshly isolated human PBMC as effectors, cetuximab was found to significantly mediate chromium-release above that seen when using the CD20-specific humanized mAb Rituxan.

Example of Therapeutic Use of EGFRt+ T Cells

Figure 10:
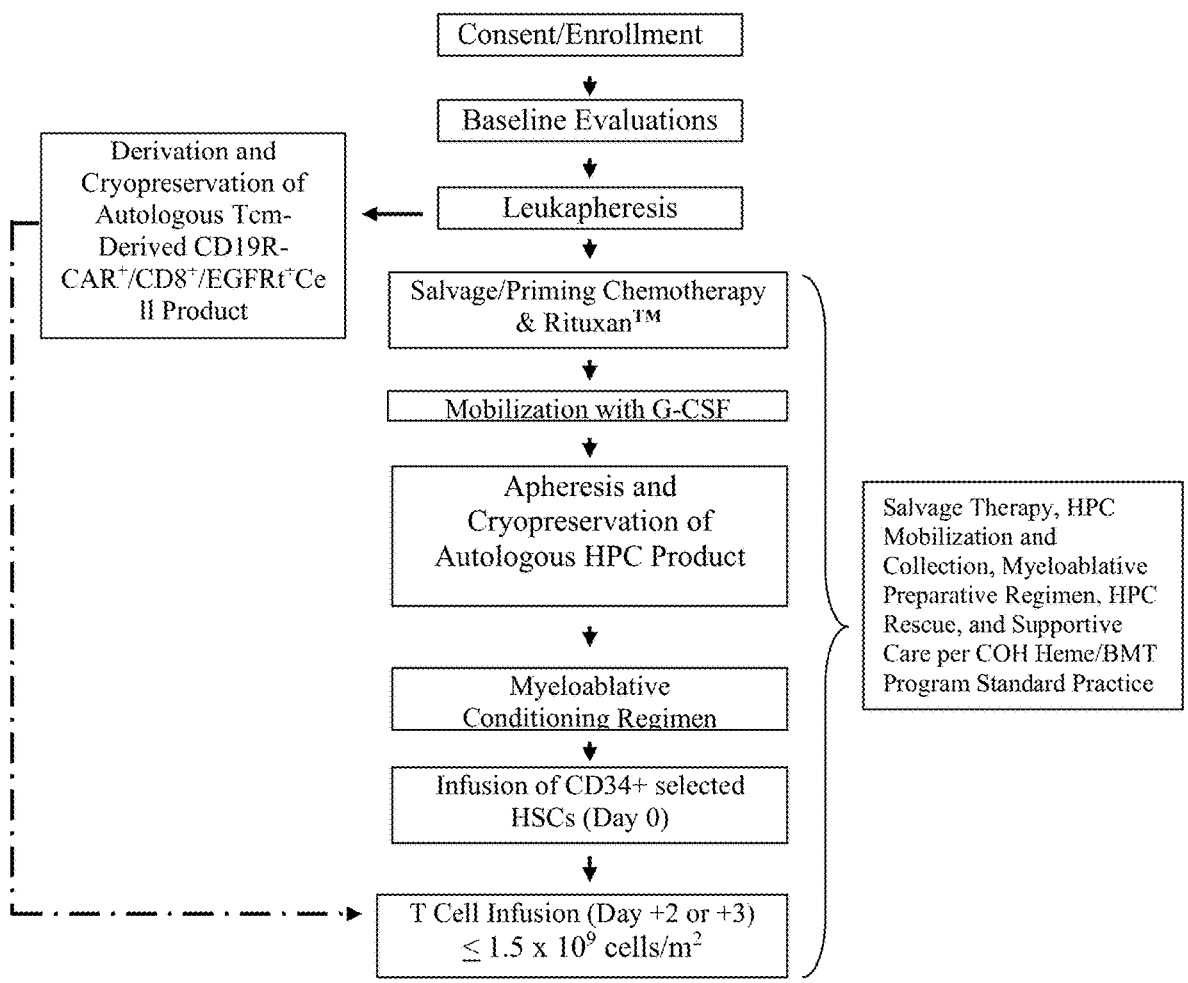
FIG. 10 is a schema showing a possible process flow for clinical trials for testing products of the present disclosure.

Adult subjects with high-risk intermediate grade B-cell lymphomas who are candidates for an autologous myeloablative stem cell transplant procedure may receive post-transplant immunotherapy with adoptively transferred autologous Tcm-derived CD19R+ CD8+ EGFRt+ T cell grafts. A leukapheresis product collected from each patient undergoes selection of Tcm, transduction with clinical grade CD19CAR-T2A-EGFRt_epHIV7, and then selection and expansion of the EGFRt+ cells in a closed system. After the resulting cell products have undergone quality control testing (including sterility and tumor specific cytotoxicity tests), they are cryopreserved. Meanwhile, following leukapheresis, study participants commence with standard salvage chemotherapy, with mobilization for auto HSC collection with cytoreductive chemotherapy and G-CSF. Since the EGFRt-selected, CD19-specific T cells will also target normal CD20+ (CD19+) B cells, the B cell numbers can first be lowered using Rituximab™ to reduce the recipient's inflammatory response upon receiving the genetically modified CTL and also increase availability of infused T cells to immediately target lymphoma cells. Furthermore, Rituximab™ may blunt a humoral immune response against the genetically modified T cells. If Rituximab™ is not given as part of the Salvage/Priming chemotherapy regimen, research participants may receive a single intravenous infusion of Rituximab™ (chimeric anti-CD20 antibody) at 375 mg/m$^2$ within 4-weeks of the planned auto-HSCT procedure. Rituximab™ infusion would be carried out per standard practice including premedication with diphenhydramine and acetaminophen and hydrocortisone. On Day +2 or Day +3 after HSCT, the autologous cryopreserved CD19R+ CD8+ EGFRt+ T cell product will be transported, thawed and infused at the patient's bedside. Research participants can be pre-medicated at least 30 minutes prior to T cell infusion with 15 mg/kg of acetaminophen P.O. (max. 650 mg) and diphenhydramine 0.5-1 mg/kg I.V. (max dose 50 mg). Clinical and laboratory correlative follow-up studies can then be performed at the physician's discretion, and may include quantitative RT-PCR studies for the presence of CD19-expressing lymphoma cells and/or the adoptively transferred T cells; FDG-PET and/or CT scans; bone marrow examination for disease specific pathologic evaluation; lymph node biopsy; and/or long-term follow up per the guidelines set forth by the FDA's Biologic Response Modifiers Advisory Committee that apply to gene transfer studies. FIG. 10 provides a possible schematic for clinical testing of the present products and methods.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All patents, patent applications, and references cited throughout the specification are expressly incorporated by reference.

REFERENCES

1. Berger, C, Flowers, M E, Warren, E H, and Riddell, S R (2006). Analysis of transgene-specific immune responses that limit the in vivo persistence of adoptively transferred HSV-TK-modified donor T cells after allogeneic hematopoietic cell transplantation. *Blood* 107: 2294-302.
2. Tey, S K, Dotti, G, Rooney, C M, Heslop, H E, and Brenner, M K (2007). Inducible caspase 9 suicide gene to improve the safety of alloddepleted T cells after haploidentical stem cell transplantation. *Biol Blood Marrow Transplant* 13: 913-24.
3. Fehse, B, Richters, A, Putimtseva-Scharf, K, Klump, H, Li, Z, Ostertag, W, et al. (2000). CD34 splice variant: an attractive marker for selection of gene-modified cells. *Mol Ther* 1: 448-56.
4. Gaines, P, and Wojchowski, D M (1999). pIRES-CD4t, a dicistronic expression vector for MACS- or FACS-based selection of transfected cells. *Biotechniques* 26: 683-8.

5. Fehse, B, Uhde, A, Fehse, N, Eckert, H G, Clausen, J, Ruger, R, et al. (1997). Selective immunoaffinity-based enrichment of CD34+ cells transduced with retroviral vectors containing an intracytoplasmatically truncated version of the human low-affinity nerve growth factor receptor (deltaLNGFR) gene. *Hum Gene Ther* 8: 1815-24.
6. Lemoine, F M, Mesel-Lemoine, M, Cherai, M, Gallot, G, Vie, H, Leclercq, V, et al. (2004). Efficient transduction and selection of human T-lymphocytes with bicistronic Thy1/HSV1-TK retroviral vector produced by a human packaging cell line. *J Gene Med* 6: 374-86.
7. Li, S, Schmitz, K R, Jeffrey, P D, Wiltzius, J J, Kussie, P, and Ferguson, K M (2005). Structural basis for inhibition of the epidermal growth factor receptor by cetuximab. *Cancer Cell* 7: 301-11.
8. Dawson, J P, Berger, M B, Lin, C C, Schlessinger, J, Lemmon, M A, and Ferguson, K M (2005). Epidermal growth factor receptor dimerization and activation require ligand-induced conformational changes in the dimer interface. *Mol Cell Biol* 25: 7734-42.
9. Lange, C, Li, Z, Fang, L, Baum, C, and Fehse, B (2007). CD34 modulates the trafficking behavior of hematopoietic cells in vivo. *Stem Cells Dev* 16: 297-304.
10. Kowolik, C M, Topp, M S, Gonzalez, S, Pfeiffer, T, Olivares, S, Gonzalez, N, et al. (2006). CD28 costimulation provided through a CD19-specific chimeric antigen receptor enhances in vivo persistence and antitumor efficacy of adoptively transferred T cells. *Cancer Res* 66: 10995-1004.
11. Szymczak, A L, Workman, C J, Wang, Y, Vignali, K M, Dilioglou, S, Vanin, E F, et al. (2004). Correction of multi-gene deficiency in vivo using a single 'self-cleaving' 2A peptide-based retroviral vector. *Nat Biotechnol* 22: 589-94.
12. Yam, P, Jensen, M, Akkina, R, Anderson, J, Villacres, M C, Wu, J, et al. (2006). Ex vivo selection and expansion of cells based on expression of a mutated inosine monophosphate dehydrogenase 2 after HIV vector transduction: effects on lymphocytes, monocytes, and CD34+ stem cells. *Mol Ther* 14: 236-44.
13. Pelloquin, F, Lamelin, J P, and Lenoir, G M (1986). Human B lymphocytes immortalization by Epstein-Barr virus in the presence of cyclosporin A. *In Vitro Cell Dev Biol* 22: 689-94.

The invention claimed is:

1. A population of human T-cells transfected with a genetically modified Epidermal Growth Factor Receptor (EGFR) gene, said gene comprising a nucleotide sequence encoding a truncated non-immunogenic endogenous cell surface molecule, said cell surface molecule comprising an EGFR Domain III and an EGFR Domain IV; but lacking all of the domains consisting of an EGFR Domain I, an EGFR Domain II, an EGFR Juxtamembrane Domain, and an EGFR Tyrosine Kinase Domain; wherein the truncated non-immunogenic endogenous cell surface molecule (i) does not have endogenous signaling or trafficking function; (ii) binds a therapeutic anti-EGFR antibody; (iii) does not bind an endogenous EGFR ligand; and (iv) acts as a marker.

2. The T-cells of claim 1, wherein the genetically modified EGFR gene comprises nucleotides 67-1071 of SEQ ID NO:2.

3. The T-cells of claim 1, wherein the genetically modified EGFR gene encodes an amino acid sequence comprising residues 23-357 of SEQ ID NO:3.

4. The T-cells of claim 1, wherein the genetically modified EGFR gene further comprises a GMCSFR alpha chain signal sequence.

5. The T-cells of claim 4, wherein the genetically modified EGFR gene comprises SEQ ID NO:2.

6. The T-cells of claim 4, wherein the genetically modified EGFR gene comprises SEQ ID NO:2.

7. The T-cells of claim 4, wherein the genetically modified EGFR gene encodes an amino acid sequence comprising at least 90% identical to SEQ ID NO:3.

8. The T-cells of claim 4, wherein the genetically modified EGFR gene encodes an amino acid sequence comprising SEQ ID NO:3.

9. The T-cells of claim 1, wherein the genetically modified EGFR gene is inserted into a vector to transfect the population of human T-cells.

10. The T-cells of claim 1, wherein the marker is used to enrich cells, to select cells, to deplete cells expressing the cell surface molecule, or to induce cell suicide in cells expressing the cell surface molecule.

11. The T-cells of claim 1, wherein the gene is part of a construct which comprises the modified EGFR coupled via a C-terminal 2A cleavable linker to a chimeric antigen receptor specific for a tumor associated antigen selected from CD19, a codon-optimized anti-CD19 costimulatory chimeric antigen receptor (CD19CAR), CD20 or CD22.

12. The T-cells of claim 11, wherein the modified EGFR is coupled to a CD19CAR and a C-terminal 2A cleavable linker.

13. A population of human T-cells transfected with a genetically modified Epidermal Growth Factor Receptor (EGFR) gene that is coupled to a CD19CAR and a C-terminal 2A cleavable linker, wherein the T-cells encode an amino acid sequence comprising SEQ ID NO:6.

14. The T-cells of claim 13, wherein the genetically modified EGFR gene is expressed by the T-cells and is used as a marker to select or enrich cells.

15. The T-cells of claim 13, wherein the genetically modified EGFR gene is expressed by the T-cells and is used as a marker to induce cell suicide.

16. The T-cells of claim 13, wherein the genetically modified EGFR gene is expressed by the T-cells and is used as a marker to deplete cells.

17. The T-cells of claim 13, wherein the genetically modified EGFR gene is inserted into a vector to transfect the population of human T-cells.

18. A population of human T-cells transfected with a genetically modified Epidermal Growth Factor Receptor (EGFR) gene, said gene comprising a nucleotide sequence encoding a truncated non-immunogenic endogenous cell surface molecule, said cell surface molecule comprising an EGFR Domain III and an EGFR Domain IV; but lacking all of the domains consisting of an EGFR Domain I, an EGFR Domain II, an EGFR Juxtamembrane Domain, and an EGFR Tyrosine Kinase Domain; wherein the truncated non-immunogenic endogenous cell surface molecule (i) does not have endogenous signaling or trafficking function; (ii) binds a therapeutic anti-EGFR antibody; (iii) does not bind an endogenous EGFR ligand; and (iv) acts as a marker to enrich cells, to select cells, to deplete cells expressing said cell surface molecule, or to induce cell suicide in cells expressing said cell surface molecule.

19. The T-cells of claim 18, wherein the therapeutic anti-EGFR antibody is cetuximab.

20. The T-cells of claim 18, wherein the genetically modified EGFR gene is inserted into a vector to transfect the population of human T-cells.

* * * * *

UNITED STATES PATENT AND TRADEMARK OFFICE
CERTIFICATE OF CORRECTION

| | |
|---|---|
| PATENT NO. | : 11,155,783 B2 |
| APPLICATION NO. | : 16/160944 |
| DATED | : October 26, 2021 |
| INVENTOR(S) | : Michael C. Jensen |

It is certified that error appears in the above-identified patent and that said Letters Patent is hereby corrected as shown below:

On the Title Page

Item (54) Title, Column 1, Line 1, delete "EPIDERIMAL" and insert -- EPIDERMAL --

Column 2, Line 17, under item (56) "OTHER PUBLICATIONS", delete "Hematoppoietic" and insert -- Hematopoietic --

Column 2, Line 23, under item (56) "OTHER PUBLICATIONS", before "Conformational", delete "Induced"

In the Specification

Column 1, Line 1, delete "EPIDERIMAL" and insert -- EPIDERMAL --

Signed and Sealed this
Seventeenth Day of January, 2023

Katherine Kelly Vidal
*Director of the United States Patent and Trademark Office*

SEQUENCE LISTING

<160> NUMBER OF SEQ ID NOS: 6

<210> SEQ ID NO 1
<211> LENGTH: 1071
<212> TYPE: DNA
<213> ORGANISM: Homo sapiens

<400> SEQUENCE: 1

```
atgcttctcc tggtgacaag ccttctgctc tgtgagttac cacacccagc attcctcctg      60
atcccacgca aagtgtgtaa cggaataggt attggtgaat ttaaagactc actctccata     120
aatgctacga atattaaaca cttcaaaaac tgcacctcca tcagtggcga tctccacatc     180
ctgccggtgg catttagggg tgactccttc acacatactc ctcctctgga tccacaggaa     240
ctggatattc tgaaaaccgt aaaggaaatc acagggtttt tgctgattca ggcttggcct     300
gaaaacagga cggacctcca tgcctttgag aacctagaaa tcatacgcgg caggaccaag     360
caacatggtc agtttttctct tgcagtcgtc agcctgaaca taacatcctt gggattacgc     420
tccctcaagg agataagtga tggagatgtg ataatttcag gaaacaaaaa tttgtgctat     480
gcaaatacaa taaactggaa aaaactgttt gggacctccg gtcagaaaac caaaattata     540
agcaacagag gtgaaaacag ctgcaaggcc acaggccagg tctgccatgc cttgtgctcc     600
cccgagggct gctggggccc ggagcccagg gactgcgtct cttgccggaa tgtcagccga     660
ggcagggaat gcgtggacaa gtgcaacctt ctggagggtg agccaaggga gtttgtggag     720
aactctgagt gcatacagtg ccacccagag tgcctgcctc aggccatgaa catcacctgc     780
acaggacggg gaccagacaa ctgtatccag tgtgcccact acattgacgg cccccactgc     840
gtcaagacct gcccggcagg agtcatggga gaaaacaaca cctggtctg gaagtacgca     900 gacgccggcc atgtgtgcca cctgtgccat ccaaactgca cctacggatg cactgggcca     960
ggtcttgaag ctgtccaac gaatgggcct aagatcccgt ccatcgccac tgggatggtg    1020
ggggccctcc tcttgctgct ggtggtggcc ctggggatcg gcctcttcat g             1071
```

<210> SEQ ID NO 2
<211> LENGTH: 1071
<212> TYPE: DNA

-continued

<213> ORGANISM: Homo sapiens

<400> SEQUENCE: 2

```
tacgaagagg accactgttc ggaagacgag acactcaatg gtgtgggtcg taaggaggac      60
tagggtgcgt ttcacacatt gccttatcca taaccactta aatttctgag tgagaggtat     120
ttacgatgct tataatttgt gaagtttttg acgtggaggt agtcaccgct agaggtgtag     180
gacggccacc gtaaatcccc actgaggaag tgtgtatgag gaggagacct aggtgtcctt     240
gacctataag acttttggca tttcctttag tgtcccaaaa acgactaagt ccgaaccgga     300
cttttgtcct gcctggaggt acggaaactc ttggatcttt agtatgcgcc gtcctggttc     360
gttgtaccag tcaaaagaga acgtcagcag tcggacttgt attgtaggaa ccctaatgcg     420
agggagttcc tctattcact acctctacac tattaaagtc ctttgttttt aaacacgata     480
cgtttatgtt atttgacctt ttttgacaaa ccctggaggc cagtcttttg gttttaatat     540
tcgttgtctc cacttttgtc gacgttccgg tgtccggtcc agacggtacg gaacacgagg     600
gggctcccga cgaccccggg cctcgggtcc ctgacgcaga gaacggcctt acagtcggct     660
ccgtccctta cgcacctgtt cacgttggaa gacctcccac tcggttccct caaacacctc     720
ttgagactca cgtatgtcac ggtgggtctc acggacggag tccggtactt gtagtggacg     780
tgtcctgccc ctggtctgtt gacataggtc acacgggtga tgtaactgcc gggggtgacg     840
cagttctgga cgggccgtcc tcagtaccct cttttgttgt gggaccagac cttcatgcgt     900
ctgcggccgg tacacacggt ggacacggta ggtttgacgt ggatgcctac gtgacccggt     960
ccagaacttc cgacaggttg cttacccgga ttctagggca ggtagcggtg accctaccac    1020
ccccgggagg agaacgacga ccaccaccgg gacccctagc cggagaagta c             1071
```

<210> SEQ ID NO 3
<211> LENGTH: 357
<212> TYPE: PRT
<213> ORGANISM: Homo sapiens

<400> SEQUENCE: 3

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
```

```
                         165                 170                 175
Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355

<210> SEQ ID NO 4
<211> LENGTH: 3186
<212> TYPE: DNA
<213> ORGANISM: Homo sapiens

<400> SEQUENCE: 4
atgctgctgc tggtgaccag cctgctgctg tgcgagctgc ccacccccgc ctttctgctg      60
atccccgaca tccagatgac ccagaccacc tccagcctga cgccagcct gggcgaccgg      120
gtgaccatca gctgccgggc cagccaggac atcagcaagt acctgaactg gtatcagcag     180
aagcccgacg gcaccgtcaa gctgctgatc taccacacca gccggctgca cagcggcgtg     240
cccagccggt ttagcggcag cggctccggc accgactaca gcctgaccat ctccaacctg     300
gaacaggaag atatcgccac ctacttttgc cagcagggca cacactgcc ctacaccttt      360
ggcggcggaa caaagctgga aatcaccggc agcacctccg gcagcggcaa gcctggcagc     420
ggcgagggca gcaccaaggg cgaggtgaag ctgcaggaaa gcggccctgg cctggtggcc     480
cccagccaga gcctgagcgt gacctgcacc gtgagcggcg tgagcctgcc cgactacggc     540
gtgagctgga tccggcagcc ccccaggaag ggcctggaat ggctgggcgt gatctggggc     600
agcgagacca cctactacaa cagcgccctg aagagccggc tgaccatcat caaggacaac     660
agcaagagcc aggtgttcct gaagatgaac agcctgcaga ccgacgacac cgccatctac     720
tactgcgcca gcactacta ctacggcggc agctacgcca tggactactg gggccagggc      780
accagcgtga ccgtgagcag cgagagcaag tacggccctc cctgcccccc ttgccctgcc     840
cccgagttcc tgggcggacc cagcgtgttc ctgttccccc caagcccaa ggacaccctg      900
atgatcagcc ggacccccga ggtgacctgc gtggtggtgg acgtgagcca ggaagatccc     960
gaggtccagt tcaattggta cgtggacggc gtggaagtgc acaacgccaa gaccaagccc    1020
```

| | |
|---|---|
| agagaggaac agttcaacag cacctaccgg gtggtgtctg tgctgaccgt gctgcaccag | 1080 |
| gactggctga acggcaaaga atacaagtgc aaggtgtcca acaagggcct gcccagcagc | 1140 |
| atcgaaaaga ccatcagcaa ggccaagggc cagcctcgcg agcccaggt gtacaccctg | 1200 |
| cctccctccc aggaagagat gaccaagaac caggtgtccc tgacctgcct ggtgaagggc | 1260 |
| ttctacccca gcgacatcgc cgtggagtgg gagagcaacg gccagcctga gaacaactac | 1320 |
| aagaccaccc ctcccgtgct ggacagcgac ggcagcttct cctgtacag ccggctgacc | 1380 |
| gtggacaaga gccggtggca ggaaggcaac gtctttagct gcagcgtgat gcacgaggcc | 1440 |
| ctgcacaacc actacaccca gaagagcctg agcctgtccc tgggcaagat gttctgggtg | 1500 |
| ctggtggtgg tgggcggggt gctggcctgc tacagcctgc tggtgacagt ggccttcatc | 1560 |
| atcttttggg tgcggagcaa gcggagcaga ggcggccaca gcgactacat gaacatgacc | 1620 |
| cccagacggc ctggccccac ccggaagcac taccagccct acgcccacc cagggactttt | 1680 |
| gccgcctacc ggtccggcgg agggcgggtg aagttcagca gaagcgccga cgcccctgcc | 1740 |
| taccagcagg gccagaatca gctgtacaac gagctgaacc tgggcagaag ggaagagtac | 1800 |
| gacgtcctgg ataagcggag aggccgggac cctgagatgg gcggcaagcc tcggcggaag | 1860 |
| aaccccagg aaggcctgta taacgaactg cagaaagaca gatggccga ggcctacagc | 1920 |
| gagatcggca tgaagggcga gcggaggcgg ggcaagggcc acgacggcct gtatcagggc | 1980 |
| ctgtccaccg ccaccaagga tacctacgac gccctgcaca tgcaggccct gccccaagg | 2040 |
| ctcgagggcg gcgagaggg cagaggaagt cttctaacat gcggtgacgt ggaggagaat | 2100 |
| cccggcccta ggatgcttct cctggtgaca agccttctgc tctgtgagtt accacaccca | 2160 |
| gcattcctcc tgatcccacg caaagtgtgt aacggaatag gtattggtga atttaaagac | 2220 |
| tcactctcca taaatgctac gaatattaaa cacttcaaaa actgcacctc catcagtggc | 2280 |
| gatctccaca tcctgccggt ggcatttagg ggtgactcct tcacacatac tcctcctctg | 2340 |
| gatccacagg aactggatat tctgaaaacc gtaaggaaa tcacagggtt tttgctgatt | 2400 |
| caggcttggc ctgaaaaacag gacggacctc catgcctttg agaacctaga aatcatacgc | 2460 |
| ggcaggacca agcaacatgg tcagtttttct cttgcagtcg tcagcctgaa cataacatcc | 2520 |
| ttgggattac gctccctcaa ggagataagt gatggagatg tgataatttc aggaaacaaa | 2580 |
| aatttgtgct atgcaaatac aataaactgg aaaaaactgt ttgggacctc cggtcagaaa | 2640 |
| accaaaatta taagcaacag aggtgaaaac agctgcaagg ccacaggcca ggtctgccat | 2700 |
| gccttgtgct cccccgaggg ctgctggggc ccggagccca gggactgcgt ctcttgccgg | 2760 |
| aatgtcagcc gaggcaggga atgcgtggac aagtgcaacc ttctggaggg tgagccaagg | 2820 |
| gagtttgtgg agaactctga gtgcatacag tgccacccag agtgcctgcc tcaggccatg | 2880 |
| aacatcacct gcacaggacg gggaccagac aactgtatcc agtgtgccca ctacattgac | 2940 |
| ggcccccact cgtcaagac ctgcccggca ggagtcatgg agaaaacaa caccctggtc | 3000 |
| tggaagtacg cagacgccgg ccatgtgtgc cacctgtgcc atccaaactg cacctacgga | 3060 |
| tgcactgggc caggtcttga aggctgtcca acgaatgggc ctaagatccc gtccatcgcc | 3120 |
| actgggatgg tgggggcccct cctcttgctg ctggtggtgg ccctggggat cggcctcttc | 3180 |
| atgtga | 3186 |

<210> SEQ ID NO 5
<211> LENGTH: 3186
<212> TYPE: DNA

<213> ORGANISM: Homo sapiens

<400> SEQUENCE: 5

| | | | | | |
|---|---|---|---|---|---|
| tacgacgacg | accactggtc | ggacgacgac | acgctcgacg | gggtggggcg | gaaagacgac | 60 |
| taggggctgt | aggtctactg | ggtctggtgg | aggtcggact | cgcggtcgga | cccgctggcc | 120 |
| cactggtagt | cgacggcccg | gtcggtcctg | tagtcgttca | tggacttgac | catagtcgtc | 180 |
| ttcgggctgc | cgtggcagtt | cgacgactag | atggtgtggt | cggccgacgt | gtcgccgcac | 240 |
| gggtcggcca | aatcgccgtc | gccgaggccg | tggctgatgt | cggactggta | gaggttggac | 300 |
| cttgtccttc | tatagcggtg | gatgaaaacg | gtcgtcccgt | tgtgtgacgg | gatgtggaaa | 360 |
| ccgccgcctt | gtttcgacct | ttagtggccg | tcgtggaggc | cgtcgccgtt | cggaccgtcg | 420 |
| ccgctcccgt | cgtggttccc | gctccacttc | gacgtccttt | cgccgggacc | ggaccaccgg | 480 |
| gggtcggtct | cggactcgca | ctggacgtgg | cactcgccgc | actcggacgg | gctgatgccg | 540 |
| cactcgacct | aggccgtcgg | ggggtccttc | ccggacctta | ccgacccgca | ctagaccccg | 600 |
| tcgctctggt | ggatgatgtt | gtcgcgggac | ttctcggccg | actggtagta | gttcctgttg | 660 |
| tcgttctcgg | tccacaagga | cttctacttg | tcggacgtct | ggctgctgtg | gcggtagatg | 720 |
| atgacgcggt | tcgtgatgat | gatgccgccg | tcgatgcggt | acctgatgac | cccggtcccg | 780 |
| tggtcgcact | ggcactcgtc | gctctcgttc | atgccgggag | ggacgggggg | aacgggacgg | 840 |
| gggctcaagg | acccgcctgg | gtcgcacaag | gacaagggg | ggttcgggtt | cctgtgggac | 900 |
| tactagtcgg | cctgggggct | ccactggacg | caccaccacc | tgcactcggt | ccttctaggg | 960 |
| ctccaggtca | agttaaccat | gcacctgccg | caccttcacg | tgttgcggtt | ctggttcggg | 1020 |
| tctctccttg | tcaagttgtc | gtggatggcc | caccacagac | acgactggca | cgacgtggtc | 1080 |
| ctgaccgact | tgccgtttct | tatgttcacg | ttccacaggt | tgttcccgga | cgggtcgtcg | 1140 |
| tagcttttct | ggtagtcgtt | ccggttcccg | gtcggagcgc | tcggggtcca | catgtgggac | 1200 |
| ggagggaggg | tccttctcta | ctggttcttg | gtccacaggg | actggacgga | ccacttcccg | 1260 |
| aagatggggt | cgctgtagcg | gcacctcacc | ctctcgttgc | cggtcggact | cttgttgatg | 1320 |
| ttctggtggg | gagggcacga | cctgtcgctg | ccgtcgaaga | aggacatgtc | ggccgactgg | 1380 |
| cacctgttct | cggccaccgt | ccttccgttg | cagaaatcga | cgtcgcacta | cgtgctccgg | 1440 |
| gacgtgttgg | tgatgtgggt | cttctcggac | tcggacaggg | acccgttcta | caagacccac | 1500 |
| gaccaccacc | acccgcccca | cgaccggacg | atgtcggacg | accactgtca | ccggaagtag | 1560 |
| tagaaaaccc | acgcctcgtt | cgcctcgtct | ccgccggtgt | cgctgatgta | cttgtactgg | 1620 |
| gggtctgccg | gaccggggtg | ggccttcgtg | atggtcggga | tgcggggtgg | gtccctgaaa | 1680 |
| cggcggatgg | ccaggccgcc | tcccgcccac | ttcaagtcgt | cttcgcggct | gcggggacgg | 1740 |
| atggtcgtcc | cggtcttagt | cgacatgttg | ctcgacttgg | acccgtcttc | ccttctcatg | 1800 |
| ctgcaggacc | tattcgcctc | tccggccctg | ggactctacc | cgccgttcgg | agccgccttc | 1860 |
| ttgggggtcc | ttccggacat | attgcttgac | gtctttctgt | tctaccggct | ccggatgtcg | 1920 |
| ctctagccgt | acttcccgct | cgcctccgcc | ccgttcccgg | tgctgccgga | catagtcccg | 1980 |
| gacaggtggc | ggtggttcct | atggatgctg | cggacgtgt | acgtccggga | cggggttcc | 2040 |
| gagctcccgc | cgcctctccc | gtctccttca | gaagattgta | cgccactgca | cctcctctta | 2100 |
| gggccgggat | cctacgaaga | ggaccactgt | tcggaagacg | agacactcaa | tggtgtgggt | 2160 |
| cgtaaggagg | actagggtgc | gtttcacaca | ttgccttatc | cataaccact | taaatttctg | 2220 |
| agtgagaggt | atttacgatg | cttataattt | gtgaagtttt | tgacgtggag | gtagtcaccg | 2280 |

```
ctagaggtgt aggacggcca ccgtaaatcc ccactgagga agtgtgtatg aggaggagac    2340
ctaggtgtcc ttgacctata agacttttgg catttccttt agtgtcccaa aaacgactaa    2400
gtccgaaccg gactttttgtc ctgcctggag gtacggaaac tcttggatct ttagtatgcg   2460
ccgtcctggt tcgttgtacc agtcaaaaga gaacgtcagc agtcggactt gtattgtagg    2520
aaccctaatg cgagggagtt cctctattca ctacctctac actattaaag tcctttgttt    2580
ttaaacacga tacgtttatg ttatttgacc ttttttgaca aaccctggag gccagtcttt    2640
tggttttaat attcgttgtc tccacttttg tcgacgttcc ggtgtccggt ccagacggta    2700
cggaacacga gggggctccc gacgaccccg ggcctcgggt ccctgacgca gagaacggcc    2760
ttacagtcgg ctccgtccct tacgcacctg ttcacgttgg aagacctccc actcggttcc    2820
ctcaaacacc tcttgagact cacgtatgtc acggtgggtc tcacggacgg agtccggtac    2880
ttgtagtgga cgtgtcctgc ccctggtctg ttgacatagg tcacacgggt gatgtaactg    2940 ccggggggtga cgcagttctg gacgggccgt cctcagtacc ctcttttgtt gtgggaccag   3000
accttcatgc gtctgcggcc ggtacacacg gtggacacgg taggtttgac gtggatgcct    3060
acgtgacccg gtccagaact tccgacaggt tgcttacccg gattctaggg caggtagcgg    3120
tgaccctacc accccgggaa ggagaacgac gaccaccacc gggacccccta gccggagaag   3180 tacact                                                              3186

<210> SEQ ID NO 6
<211> LENGTH: 1061
<212> TYPE: PRT
<213> ORGANISM: Homo sapiens

<400> SEQUENCE: 6

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205
```

```
Ala Leu Lys Ser Arg Leu Thr Ile Ile Lys Asp Asn Ser Lys Ser Gln
        210                 215                 220
Val Phe Leu Lys Met Asn Ser Leu Gln Thr Asp Asp Thr Ala Ile Tyr
225                 230                 235                 240
Tyr Cys Ala Lys His Tyr Tyr Tyr Gly Gly Ser Tyr Ala Met Asp Tyr
                245                 250                 255
Trp Gly Gln Gly Thr Ser Val Thr Val Ser Ser Glu Ser Lys Tyr Gly
            260                 265                 270
Pro Pro Cys Pro Pro Cys Pro Ala Pro Glu Phe Leu Gly Gly Pro Ser
        275                 280                 285
Val Phe Leu Phe Pro Pro Lys Pro Lys Asp Thr Leu Met Ile Ser Arg
290                 295                 300
Thr Pro Glu Val Thr Cys Val Val Val Asp Val Ser Gln Glu Asp Pro
305                 310                 315                 320
Glu Val Gln Phe Asn Trp Tyr Val Asp Gly Val Glu Val His Asn Ala
                325                 330                 335
Lys Thr Lys Pro Arg Glu Glu Gln Phe Asn Ser Thr Tyr Arg Val Val
            340                 345                 350
Ser Val Leu Thr Val Leu His Gln Asp Trp Leu Asn Gly Lys Glu Tyr
        355                 360                 365
Lys Cys Lys Val Ser Asn Lys Gly Leu Pro Ser Ser Ile Glu Lys Thr
370                 375                 380
Ile Ser Lys Ala Lys Gly Gln Pro Arg Glu Pro Gln Val Tyr Thr Leu
385                 390                 395                 400
Pro Pro Ser Gln Glu Glu Met Thr Lys Asn Gln Val Ser Leu Thr Cys
                405                 410                 415
Leu Val Lys Gly Phe Tyr Pro Ser Asp Ile Ala Val Glu Trp Glu Ser
            420                 425                 430
Asn Gly Gln Pro Glu Asn Asn Tyr Lys Thr Thr Pro Pro Val Leu Asp
        435                 440                 445
Ser Asp Gly Ser Phe Phe Leu Tyr Ser Arg Leu Thr Val Asp Lys Ser
450                 455                 460
Arg Trp Gln Glu Gly Asn Val Phe Ser Cys Ser Val Met His Glu Ala
465                 470                 475                 480
Leu His Asn His Tyr Thr Gln Lys Ser Leu Ser Leu Ser Leu Gly Lys
                485                 490                 495
Met Phe Trp Val Leu Val Val Gly Gly Val Leu Ala Cys Tyr Ser
            500                 505                 510
Leu Leu Val Thr Val Ala Phe Ile Ile Phe Trp Val Arg Ser Lys Arg
        515                 520                 525
Ser Arg Gly Gly His Ser Asp Tyr Met Asn Met Thr Pro Arg Arg Pro
530                 535                 540
Gly Pro Thr Arg Lys His Tyr Gln Pro Tyr Ala Pro Pro Arg Asp Phe
545                 550                 555                 560
Ala Ala Tyr Arg Ser Gly Gly Arg Val Lys Phe Ser Arg Ser Ala
                565                 570                 575
Asp Ala Pro Ala Tyr Gln Gln Gly Gln Asn Gln Leu Tyr Asn Glu Leu
            580                 585                 590
Asn Leu Gly Arg Arg Glu Glu Tyr Asp Val Leu Asp Lys Arg Arg Gly
        595                 600                 605
Arg Asp Pro Glu Met Gly Gly Lys Pro Arg Arg Lys Asn Pro Gln Glu
610                 615                 620
```

```
Gly Leu Tyr Asn Glu Leu Gln Lys Asp Lys Met Ala Glu Ala Tyr Ser
625                 630                 635                 640

Glu Ile Gly Met Lys Gly Glu Arg Arg Gly Lys Gly His Asp Gly
            645                 650                 655

Leu Tyr Gln Gly Leu Ser Thr Ala Thr Lys Asp Thr Tyr Asp Ala Leu
                660                 665                 670

His Met Gln Ala Leu Pro Pro Arg Leu Glu Gly Gly Glu Gly Arg
            675                 680                 685

Gly Ser Leu Leu Thr Cys Gly Asp Val Glu Glu Asn Pro Gly Pro Arg
690                 695                 700

Met Leu Leu Leu Val Thr Ser Leu Leu Leu Cys Glu Leu Pro His Pro
705                 710                 715                 720

Ala Phe Leu Leu Ile Pro Arg Lys Val Cys Asn Gly Ile Gly Ile Gly
            725                 730                 735

Glu Phe Lys Asp Ser Leu Ser Ile Asn Ala Thr Asn Ile Lys His Phe
            740                 745                 750

Lys Asn Cys Thr Ser Ile Ser Gly Asp Leu His Ile Leu Pro Val Ala
            755                 760                 765

Phe Arg Gly Asp Ser Phe Thr His Thr Pro Pro Leu Asp Pro Gln Glu
770                 775                 780

Leu Asp Ile Leu Lys Thr Val Lys Glu Ile Thr Gly Phe Leu Leu Ile
785                 790                 795                 800

Gln Ala Trp Pro Glu Asn Arg Thr Asp Leu His Ala Phe Glu Asn Leu
            805                 810                 815

Glu Ile Ile Arg Gly Arg Thr Lys Gln His Gly Gln Phe Ser Leu Ala
            820                 825                 830

Val Val Ser Leu Asn Ile Thr Ser Leu Gly Leu Arg Ser Leu Lys Glu
            835                 840                 845

Ile Ser Asp Gly Asp Val Ile Ile Ser Gly Asn Lys Asn Leu Cys Tyr
850                 855                 860

Ala Asn Thr Ile Asn Trp Lys Lys Leu Phe Gly Thr Ser Gly Gln Lys
865                 870                 875                 880

Thr Lys Ile Ile Ser Asn Arg Gly Glu Asn Ser Cys Lys Ala Thr Gly
            885                 890                 895

Gln Val Cys His Ala Leu Cys Ser Pro Glu Gly Cys Trp Gly Pro Glu
            900                 905                 910

Pro Arg Asp Cys Val Ser Cys Arg Asn Val Ser Arg Gly Arg Glu Cys
            915                 920                 925

Val Asp Lys Cys Asn Leu Leu Glu Gly Glu Pro Arg Glu Phe Val Glu
930                 935                 940

Asn Ser Glu Cys Ile Gln Cys His Pro Glu Cys Leu Pro Gln Ala Met
945                 950                 955                 960

Asn Ile Thr Cys Thr Gly Arg Gly Pro Asp Asn Cys Ile Gln Cys Ala
            965                 970                 975

His Tyr Ile Asp Gly Pro His Cys Val Lys Thr Cys Pro Ala Gly Val
            980                 985                 990

Met Gly Glu Asn Asn Thr Leu Val Trp Lys Tyr Ala Asp Ala Gly His
            995                 1000                1005

Val Cys His Leu Cys His Pro Asn Cys Thr Tyr Gly Cys Thr Gly
    1010                1015                1020

Pro Gly Leu Glu Gly Cys Pro Thr Asn Gly Pro Lys Ile Pro Ser
    1025                1030                1035
```

```
Ile Ala  Thr Gly Met Val Gly  Ala Leu Leu Leu  Leu Val Val
    1040             1045              1050

Ala Leu  Gly Ile Gly Leu Phe  Met
    1055             1060
```